US011046777B2

(12) United States Patent
Marasco et al.

(10) Patent No.: US 11,046,777 B2
(45) Date of Patent: Jun. 29, 2021

(54) GLUCOCORTICOID-INDUCED TUMOR NECROSIS FACTOR RECEPTOR (GITR) ANTIBODIES AND METHODS OF USE THEREOF

(71) Applicant: Dana-Farber Cancer Institute, Inc., Boston, MA (US)

(72) Inventors: Wayne A. Marasco, Wellesley, MA (US); Quan Karen Zhu, Southborough, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 0 days.

(21) Appl. No.: 16/319,590

(22) PCT Filed: Jul. 24, 2017

(86) PCT No.: PCT/US2017/043504
§ 371 (c)(1),
(2) Date: Jan. 22, 2019

(87) PCT Pub. No.: WO2018/018039
PCT Pub. Date: Jan. 25, 2018

(65) Prior Publication Data
US 2021/0101989 A1    Apr. 8, 2021

Related U.S. Application Data

(60) Provisional application No. 62/375,634, filed on Aug. 16, 2016, provisional application No. 62/365,712, filed on Jul. 22, 2016.

(51) Int. Cl.
   *C07K 16/28*      (2006.01)
   *A61K 39/00*      (2006.01)
   *A61K 38/20*      (2006.01)

(52) U.S. Cl.
   CPC ...... *C07K 16/2878* (2013.01); *A61K 38/2086* (2013.01); *C07K 2317/24* (2013.01); *C07K 2317/31* (2013.01); *C07K 2317/565* (2013.01); *C07K 2317/622* (2013.01); *C07K 2317/73* (2013.01); *C07K 2317/75* (2013.01); *C07K 2317/92* (2013.01)

(58) Field of Classification Search
   None
   See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,522,811 A | 6/1985 | Eppstein et al. | |
| 4,544,545 A | 10/1985 | Ryan et al. | |
| 4,676,980 A | 6/1987 | Segal et al. | |
| 4,816,567 A | 3/1989 | Cabilly et al. | |
| 5,013,556 A | 5/1991 | Woodle et al. | |
| 5,030,719 A | 7/1991 | Umemoto et al. | |
| 5,091,513 A | 2/1992 | Huston et al. | |
| 5,132,405 A | 7/1992 | Huston et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,939,598 A | 8/1999 | Kucherlapati et al. | |
| 8,709,424 B2 | 4/2014 | Schebye et al. | |

FOREIGN PATENT DOCUMENTS

| | | | |
|---|---|---|---|
| WO | 91/00360 | 1/1991 | |
| WO | 92/00373 | 1/1992 | |
| WO | 94/02602 | 2/1994 | |
| WO | 94/11026 | 5/1994 | |
| WO | 95/22618 | 8/1995 | |
| WO | 96/33735 | 10/1996 | |
| WO | 96/34096 | 10/1996 | |
| WO | 99/53049 | 10/1999 | |
| WO | 05/18572 | 3/2005 | |
| WO | 05/47327 | 5/2005 | |
| WO | 2006/105021 | 10/2006 | |
| WO | 13/39954 | 3/2013 | |
| WO | 2015/026684 | 2/2015 | |
| WO | 2015/184099 | 12/2015 | |
| WO | 2015/187835 | 12/2015 | |
| WO | 16/54638 | 4/2016 | |
| WO | WO 2016/073906 | * 5/2016 | |

OTHER PUBLICATIONS

"Conjugate Vaccines", Contributions to Microbiology and Immunology, J. M. Cruse and R. E. Lewis, Jr (eds), Carger Press, New York, (1989).
"Immunoassay", E. Diamandis and T. Christopoulus, Academic Press, Inc., San Diego, CA, 1996.
"Practice and Theory of Enzyme Immunoassays", P. Tijssen, Elsevier Science Publishers, Amsterdam, 1985.
Antibodies: A Laboratory Manual, Harlow E, and Lane D, 1988, Cold Spring Harbor Laboratory Press, Cold Spring Harbor, NY.
Barbas et al., Proc. Natl. Acad. Sci. USA 89:9339-43 (1992).
Bobo et al., Proc. Natl. Acad. Sci. USA 91:2076-2080 (1994).
Brodeur et al., Monoclonal Antibody Production Techniques and Applications, Marcel Dekker, Inc., New York, (1987) pp. 51-63.
Caron et al., J. Exp Med., 176: 1191-1195 (1992).
Cole, et al., 198S In: Monoclonal Antibodies and Cancer Therapy, Alan R. Liss, Inc., pp. 77-96.

(Continued)

*Primary Examiner* — Laura B Goddard
(74) *Attorney, Agent, or Firm* — Baker Donelson

(57) ABSTRACT

The present invention comprises human monoclonal antibodies that bind to GITR (also known as glucocorticoid-induced tumor necrosis factor receptor). Binding of the invented antibody to GITR inhibits binding of its ligand, GITR-L, and can be used to treat cancer.

27 Claims, 15 Drawing Sheets

Specification includes a Sequence Listing.

(56) References Cited

OTHER PUBLICATIONS

Cote, et al., 1983. Proc Natl Acad Sci USA 80: 2026-2030.
D. Wilkinson (The Scientist, published by the Scientist, Inc., Philadelphia PA, vol. 14, No. 8 (Apr. 17, 2000X pp. 25-28.
Davidson, et al., Nat. Genet 3:219 (1993).
Davies et al. (1990) Annual Rev Biochem 59:439-473.
ELISA: Theory and Practice: Methods in Molecular Biology, vol. 42, J. R. Crowther (Ed.) Human Press, Totowa, NJ, 1995.
Epstein et al., Proc. Natl. Acad Sci. USA, 82: 3688 (1985).
Fishwild et al, Nature Biotechnology 14, 845-51 (1996).
Geller, A I. et al., J. Neurochem, 64:487 (1995).
Geller, A. 1., et al., ProcNatl. Acad Sci USA 87:1149 (1990).
Geller, A. I. et al., ProcNatl. Acad. Sci.: U.S.A. 90:7603 (1993).
Goding, Monoclonal Antibodies: Principles and Practice. Academic Press, (1986) pp. 59-103).
Hoogenboom and Winter, J. Mol. Biol., 227:381 (1992).
Huse, et al., 1989 Science 246: 1275-1281.
Huston et al. (1988) Proc Nat Acad Sci USA 85(16):5879-5883.
Hwang et al., Proc. Natl Acad. Sci. USA, 77: 4030 (1980).
Int'l Preliminary Report on Patentability PCT/US17/43504, dated Jan. 22, 2019.
Int'l Search Report PCT/US17143504, completed Oct. 18, 2017.
Jansen et al., Immunological Reviews 62:185-216 (1982).
Kaplitt, M. G.. et al., Nat. Genet 8:148 (1994).
Killen and Lindstrom, Jour. Immun. 133:1335-2549 (1984).
Knee Deborah A et al, "Rationale for anti-GITR cancer immunotherapy", European Journal of Cancer, Elsevier, Amsterdam, NL, vol. 67, Aug. 31, 2016 (Aug. 31, 2016), p. 1-10.
Ko K. et al., Treatment of advanced tumors with agonistic anti-GITR mAb and its effects on tumor-inflitrating Foxp3+CD25+ CD4+ regulatory T cells. J Exp Med., Sep. 26, 2005, vol. 202, No. 7, pp. 885-891.
Kohler and Milstein, Nature, 256:495 (1975).
Kozbor, et al., 1983 Immunol Today 4: 72.
Kozbor, J. Immunol., 133:3001 (1984).
Labrijn, A.F. et al, 2011, Journal of Immunol 187:3238-3246.
Lam, Anticancer Drug Des., 12:145, 1997.
LeGal LaSalle et al., Science, 259:988 (1993).
Lim, F., et al., in DNA Cloning: Mammalian Systems, D. Glover, Ed. (Oxford Univ. Press, Oxford England) (1995).
Lonberg and Huszar, Intern. Rev. Immunol. 13 65-93 (1995).
Lonberg et al., Nature 368 856-859 (1994).
Malmqvist, Magnus; Nature 361: 186-87 (1993).
Marasco et al., Proc. Natl. Acad. Sci. USA, 90: 7889-7893 (1993).
Marks et al., Bio/Technology 10, 779-783 (1992).
Marks et al., J. Mol. Biol., 222:581 (1991).
Martin et al., J. Biol. Chem., 257: 286-288 (1982).
Morrison et al., Am. J. Physiol. 266:292-305 (1994).
Morrison, Nature 368, 812-13 (1994).
Munson and Pollard, Anal. Biochem, 107:220 (1980).
Neuberger, Nature Biotechnology 14, 826 (1996).
Peptide and Protein Drug Delivery (Advances in Parenteral Sciences, vol. 4), 1991, M. Dekker, New York.
Ramakrishnan, S. et al., Cancer Res. 44:201-208 (1984).
Remington: The Science and Practice of Pharmacy 19th ed. (Alfonso R Gennaro, et al., editors) Mack Pub. Co., Easton, Pa., 1995.
Ridgway et al., Protein Eng 7:617-621 (1996).
Shopes, J. Immunol., 148: 2918-2922 (1992).
Van derNeut Kolfschoten, M. et al., 2007, Science 317: 1554-1557.
Vitetta et al, Science 238: 1098 (1987).
Written Opinion, PCT/US17/43504.
Yang, et al., J. Virol. 69:2004 (1995).
Zebedee et al., Proc. Natl. Acad. Sci. USA 89:3175-79 (1992).
Schaer, David A., Adam D. Cohen, and Jedd D. Wolchok. "Anti-GITR antibodies—potential clinical applications for tumor immunotherapy." Current opinion in investigational drugs (London, England: 2000) 11.12 (2010): 1378.

* cited by examiner

Figure 1

Plate 1: Coating pattern

|   | 1 | 2 | 3 | 4 | 5 | 6 | 7 | 8 | 9 | 10 | 11 | 12 |
|---|---|---|---|---|---|---|---|---|---|----|----|----|
| A | E1-3A1 | ET1-3B1 | P3-2B8 | P4-2F8 | TT1-3C6 | TT5-3E2 | E1-3A1 | ET1-3B1 | P3-2B8 | P4-2F8 | TT1-3C6 | TT5-3E2 |
| B | E1-3B4 | ET1-3D6 | P3-2E11 | T1-3D1 | TT1-3C8 | TT5-3E5 | E1-3B4 | ET1-3D6 | P3-2E11 | T1-3D1 | TT1-3C8 | TT5-3E5 |
| C | E1-3E5 | ET1-3E12 | P3-2H7 | T1-3G7 | TT1-3D6 | TT5-3E7 | E1-3E5 | ET1-3E12 | P3-2H7 | T1-3G7 | TT1-3D6 | TT5-3E7 |
| D | E1-3E9 | ET1-3F2 | P4-2A6 | T5-3A1 | TT1-3E8 | TT5-3G3 | E1-3E9 | ET1-3F2 | P4-2A6 | T5-3A1 | TT1-3E8 | TT5-3G3 |
| E | E1-3F6 | P1-2A11 | P4-2B7 | T5-3A7 | TT1-3F5 | TT5-3H7 | E1-3F6 | P1-2A11 | P4-2B7 | T5-3A7 | TT1-3F5 | TT5-3H7 |
| F | E1-3H7 | P2-2B5 | P4-2C8 | | TT1-3F6 | 2XYT | E1-3H7 | P2-2B5 | P4-2C8 | | TT1-3F6 | 2XYT |
| G | E5-3B2 | P2-2D12 | P4-2F1 | T5-3D4 | TT1-3F9 | 2XYT | E5-3B2 | P2-2D12 | P4-2F1 | T5-3D4 | TT1-3F9 | 2XYT |
| H | 2 XYT | P2-2E10 | P4-2F2 | T5-3H11 | 2 XYT | 2 XYT | 2 XYT | P2-2E10 | P4-2F2 | T5-3H11 | 2 XYT | 2 XYT |

A. hGITR-His (200ug/ml; 50ul + 4950ulPBS) 100ul/well

B. hGITR-mIgG2a (1mg/ml; 10ul + 4990ul PBS) 100ul/well

Plate 2: Coating pattern 3. mGITR-His (400ug/ml; 25ul + 4975ulPBS) 100ul/well

D. mIgG2a (1mg/ml; 10ul + 4990ul PBS) 100ul/well

Figure 1 cont.

Plate 1

| | hGITR-His | hGITR-His | hGITR-His | hGITR-His | hGITR-His | hGITR-His | hGITR-mIG | hGITR-mIG | hGITR-mIG | hGITR-mIG | hGITR-mIG | hGITR-mIG |
|---|---|---|---|---|---|---|---|---|---|---|---|---|
| | 1 | 2 | 3 | 4 | 5 | 6 | 7 | 8 | 9 | 10 | 11 | 12 |
| A | 0.052 | 1.828 | 0.616 | 0.048 | 1.986 | 0.254 | 1.895 | 1.936 | 0.062 | 0.054 | 2.156 | 0.973 |
| B | 1.087 | 1.097 | 0.051 | 0.209 | 1.405 | 0.046 | 2.171 | 1.974 | 0.044 | 1.533 | 1.845 | 1.634 |
| C | 0.763 | 0.091 | 0.047 | 0.412 | 1.983 | 0.045 | 1.992 | 1.789 | 0.053 | 2.086 | 2.146 | 2.157 |
| D | 0.821 | 0.052 | 1.982 | 0.047 | 0.054 | 0.048 | 1.949 | 1.908 | 0.046 | 0.052 | 2.481 | 1.563 |
| E | 1.855 | 2.085 | 0.488 | 0.047 | 1.131 | 0.049 | 2.197 | 2.473 | 0.492 | 0.045 | 1.452 | 1.478 |
| F | 1.957 | 1.261 | 0.054 | 0.217 | 0.048 | 0.094 | 2.165 | 1.698 | 0.046 | 1.763 | 1.253 | 0.043 |
| G | 1.950 | 0.671 | 0.067 | 0.049 | 0.046 | 0.044 | 2.071 | 2.014 | 0.047 | 0.045 | 0.425 | 0.044 |
| H | 0.057 | 0.374 | 1.407 | 0.060 | 0.054 | 0.045 | 0.056 | 0.462 | 1.282 | 1.264 | 0.054 | 0.053 |

Plate 2

| | mGITR-His | mGITR-His | mGITR-His | mGITR-His | mGITR-His | mGITR-His | mIgG2a | mIgG2a | mIgG2a | mIgG2a | mIgG2a | mIgG2a |
|---|---|---|---|---|---|---|---|---|---|---|---|---|
| | 1 | 2 | 3 | 4 | 5 | 6 | 7 | 8 | 9 | 10 | 11 | 12 |
| A | 0.071 | 0.053 | 1.450 | 0.423 | 0.052 | 0.047 | 0.066 | 0.058 | 0.116 | 0.048 | 0.106 | 0.072 |
| B | 0.050 | 0.047 | 0.044 | 0.046 | 0.043 | 0.042 | 0.044 | 0.608 | 0.056 | 0.069 | 0.061 | 1.861 |
| C | 0.069 | 0.047 | 1.854 | 0.044 | 0.046 | 0.044 | 0.048 | 0.077 | 0.188 | 0.050 | 0.041 | 0.054 |
| D | 0.048 | 0.058 | 2.175 | 0.041 | 0.045 | 0.047 | 0.078 | 0.046 | 0.053 | 0.043 | 0.048 | 0.455 |
| E | 0.063 | 0.049 | 0.366 | 0.042 | 0.045 | 0.044 | 0.140 | 0.064 | 0.601 | 0.088 | 0.067 | 0.050 |
| F | 0.055 | 0.050 | 1.985 | 0.049 | 0.047 | 0.043 | 0.044 | 0.124 | 0.049 | 0.046 | 0.519 | 0.054 |
| G | 0.057 | 0.055 | 0.938 | 0.061 | 0.043 | 0.045 | 0.047 | 0.045 | 0.217 | 0.064 | 0.046 | 0.051 |
| H | 0.051 | 0.112 | 0.160 | 0.054 | 0.051 | 0.053 | 0.047 | 1.083 | 0.395 | 0.433 | 0.049 | 0.050 |

Figure 2
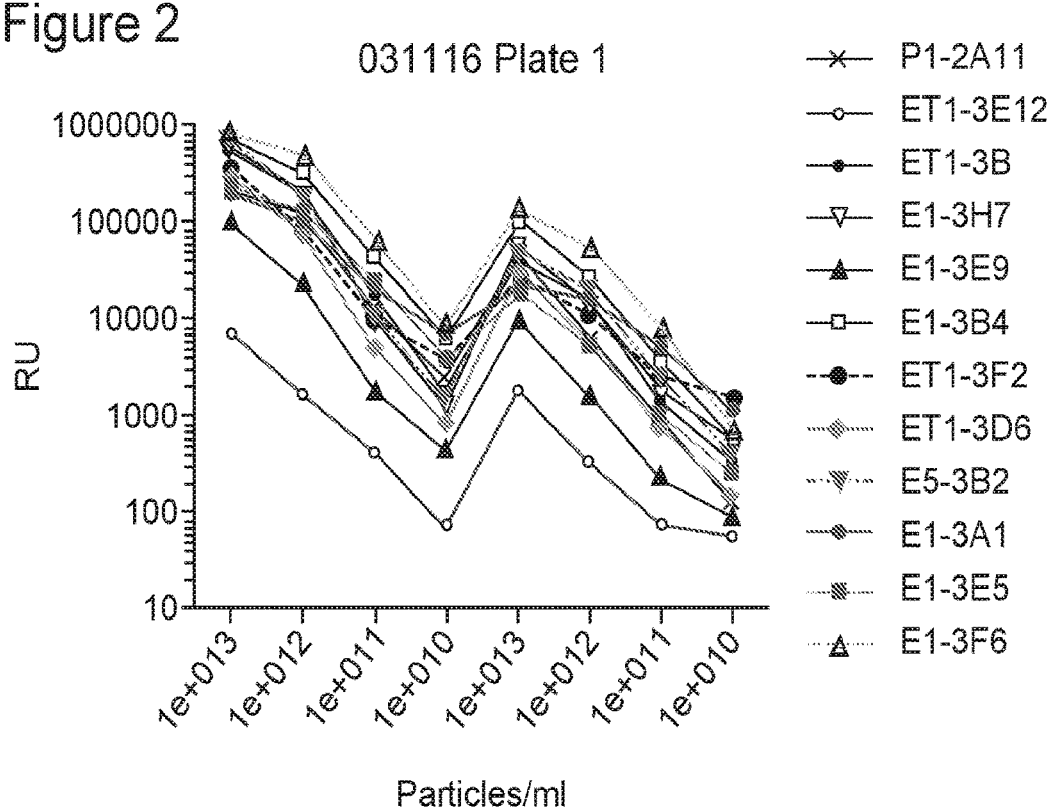
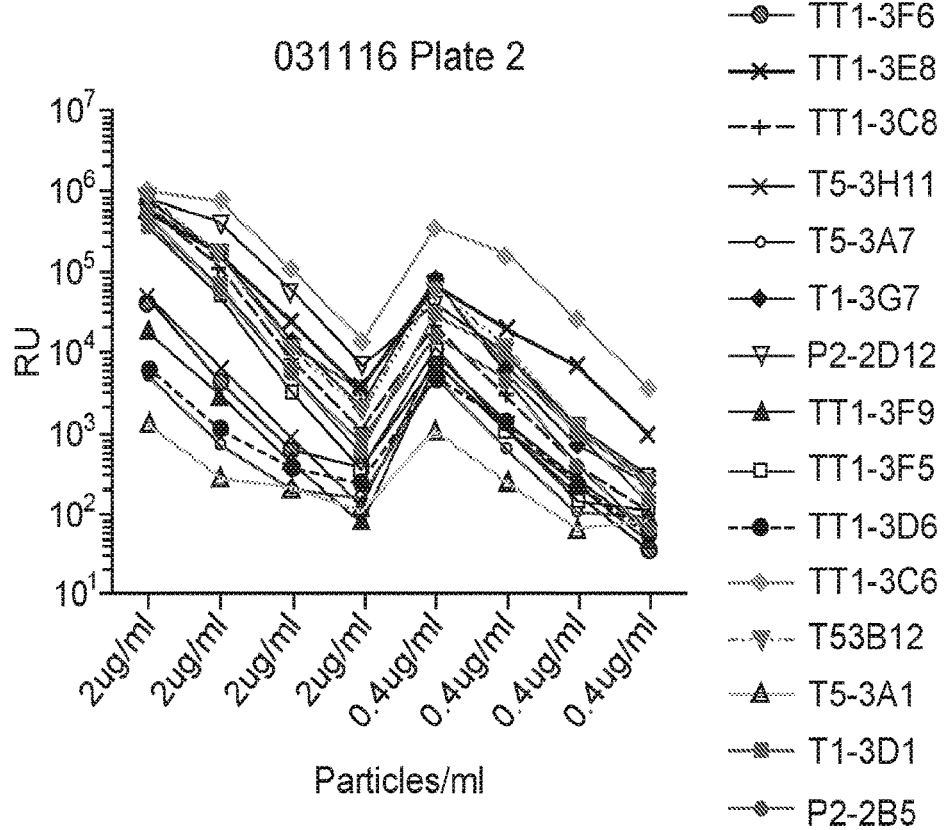

Figure 4

| | 1 | 2 | 3 | 4 | 5 | 6 | 7 | 8 | 9 | 10 | 11 | 12 |
|---|---|---|---|---|---|---|---|---|---|---|---|---|
| | | | | CL-354 (GITR stable CHO cell pool) | | | | | | CL-355 (CA9 stable CHO cell pool) | | |
| A | E1-3B4 | 4.00E+12 | 4.00E+11 | 4.00E+10 | P2-2D12 | 4.00E+12 | 4.00E+11 | 4.00E+10 | TT5-3E7 | E1-3B4 | P2-2D12 | TT5-3E7 |
| B | E1-3E5 | 4.00E+12 | 4.00E+11 | 4.00E+10 | TT1-3C6 | 4.00E+12 | 4.00E+11 | 4.00E+10 | TT5-3G3 | E1-3E5 | TT1-3C6 | TT5-3G3 |
| C | E1-3E9 | 4.00E+12 | 4.00E+11 | 4.00E+10 | TT1-3C8 | 4.00E+12 | 4.00E+11 | 4.00E+10 | TT5-3H7 | E1-3E9 | TT1-3C8 | TT5-3H7 |
| D | E1-3F6 | 4.00E+12 | 4.00E+11 | 4.00E+10 | TT1-3F5 | 4.00E+12 | 4.00E+11 | 4.00E+10 | ET1-3F2 | E1-3F6 | TT1-3F5 | ET1-3F2 |
| E | E1-3H7 | 4.00E+12 | 4.00E+11 | 4.00E+10 | P1-2A11 | 4.00E+12 | 4.00E+11 | 4.00E+10 | P4-2F2 | E1-3H7 | P1-2A11 | P4-2F2 |
| F | E5-3B2 | 4.00E+12 | 4.00E+11 | 4.00E+10 | P2-2B5 | 4.00E+12 | 4.00E+11 | 4.00E+10 | anti-GITR | E5-3B2 | P2-2B5 | anti-GITR |
| G | ET1-3B1 | 4.00E+12 | 4.00E+11 | 4.00E+10 | TT5-3E2 | 4.00E+12 | 4.00E+11 | 4.00E+10 | anti-CA9 | ET1-3B1 | TT5-3E2 | anti-CA9 |
| H | ET1-3E12 | 4.00E+12 | 4.00E+11 | 4.00E+10 | T5-3A1* | 4.00E+12 | 4.00E+11 | 4.00E+10 | anti-M13 | ET1-3E12 | T5-3A1* | anti-M13 |

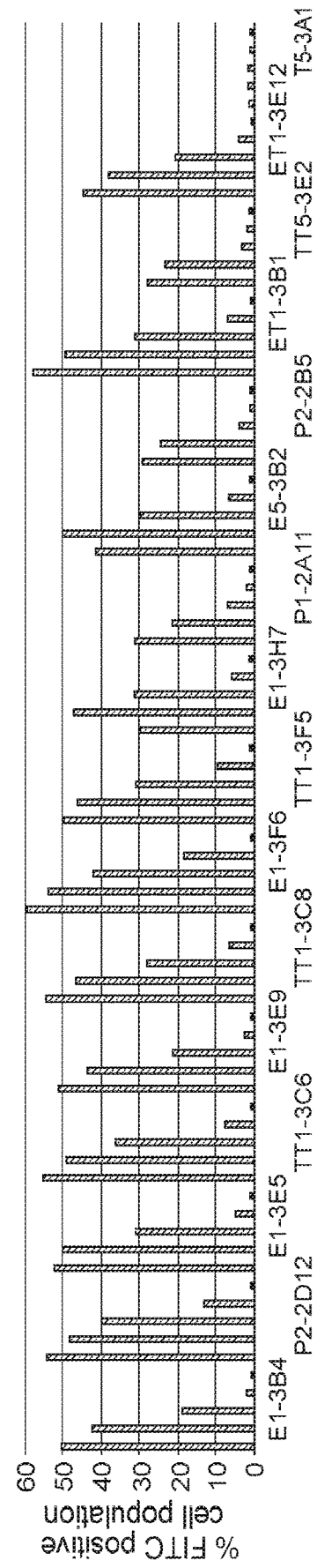

The 2nd FACS – GITR binding assay 04/07/2016

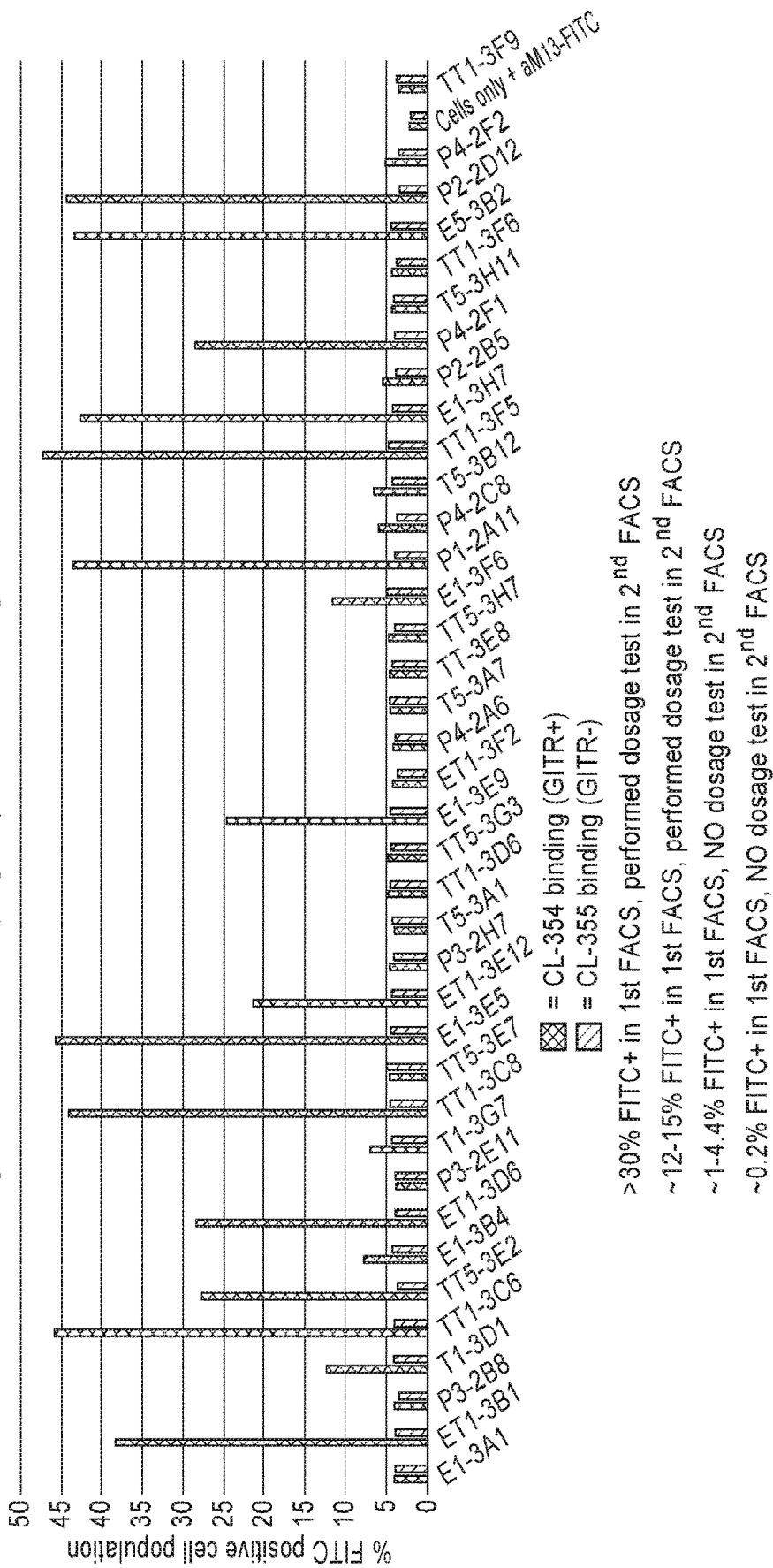

Figure 6

Plate 1 & 2 Clone map

|   | 1 | 2 | 3 | 4 | 5 | 6 | 7 | 8 | 9 | 10 | 11 | 12 |
|---|---|---|---|---|---|---|---|---|---|----|----|----|
| A | E1-3A1 | ET-3B1 | P3-2B8 | T1-3D1 | TT1-3C6 | TT5-3E2 | E1-3A1 | ET1-3B1 | P3-2B8 | T1-3D1 | TT1-3C6 | TT5-3E2 |
| B | E1-3B4 | ET1-3D6 | P3-2E11 | T1-3G7 | TT1-3C8 | TT5-3E7 | E1-3B4 | ET1-3D6 | P3-2E11 | T1-3G7 | TT1-3C8 | TT5-3E7 |
| C | E1-3E5 | ET1-3E12 | P3-2H7 | T5-3A1 | TT1-3D6 | TT5-3G3 | E1-3E5 | ET1-3E12 | P3-2H7 | T5-3A1 | TT1-3D6 | TT5-3G3 |
| D | E1-3E9 | ET1-3F2 | P4-2A6 | T5-3A7 | TT1-3E8 | TT5-3H7 | E1-3E9 | ET1-3F2 | P4-2A6 | T5-3A7 | TT1-3E8 | TT5-3H7 |
| E | E1-3F6 | P1-2A11 | P4-2C8 | T5-3B12 | TT1-3F5 |   | E1-3F6 | P1-2A11 | P4-2C8 | T5-3B12 | TT1-3F5 |   |
| F | E1-3H7 | P2-2B5 | P4-2F1 | T5-3H11 | TT1-3F6 |   | E1-3H7 | P2-2B5 | P4-2F1 | T5-3H11 | TT1-3F6 |   |
| G | E5-3B2 | P2-2D12 | P4-2F2 |   | TT1-3F9 |   | E5-3B2 | P2-2D12 | P4-2F2 |   | TT1-3F9 |   |
| H |   |   |   |   |   |   |   |   |   |   |   |   |

Plate 1: Coating pattern

|   | 1 | 2 | 3 | 4 | 5 | 6 | 7 | 8 | 9 | 10 | 11 | 12 |
|---|---|---|---|---|---|---|---|---|---|----|----|----|
| A | A. hGITR-His (2100ug/ml: 50ul + 4950ulPBS) 100ul/well | | | | | | B. hGITR-mIgG2a (1mg/ml: 10ul + 4990ul PBS) 100ul/well | | | | | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

Plate 2: Coating pattern

|   | 1 | 2 | 3 | 4 | 5 | 6 | 7 | 8 | 9 | 10 | 11 | 12 |
|---|---|---|---|---|---|---|---|---|---|----|----|----|
| A | C. hGITR-His (400ug/ml: 25ul + 4975ulPBS) 100ul/well | | | | | | B. mIgG2a (1mg/ml: 10ul + 4990ul PBS) 100ul/well | | | | | |
| B | | | | | | | | | | | | |
| C | | | | | | | | | | | | |
| D | | | | | | | | | | | | |
| E | | | | | | | | | | | | |
| F | | | | | | | | | | | | |
| G | | | | | | | | | | | | |
| H | | | | | | | | | | | | |

Figure 6 (cont.)

Plate 1 OD450

| | 1 | 2 | 3 | 4 | 5 | 6 | 7 | 8 | 9 | 10 | 11 | 12 |
|---|---|---|---|---|---|---|---|---|---|---|---|---|
| A | 0.058 | 1.593 | 0.175 | 0.148 | 1.440 | 0.217 | 1.361 | 1.340 | 0.056 | 0.779 | 1.297 | 1.025 |
| B | 0.554 | 0.834 | 0.306 | 0.131 | 0.728 | 0.076 | 1.556 | 1.341 | 0.105 | 1.205 | 1.228 | 1.328 |
| C | 0.612 | 0.073 | 0.058 | 0.065 | 0.063 | 0.063 | 1.813 | 0.709 | 0.058 | 0.057 | 0.078 | 1.029 |
| D | 0.476 | 0.078 | 0.428 | 0.056 | 0.071 | 0.056 | 1.419 | 0.706 | 0.066 | 0.073 | 0.908 | 1.665 |
| E | 1.714 | 1.286 | 0.130 | 0.186 | 1.839 | 0.053 | 1.952 | 1.663 | 0.958 | 1.085 | 1.980 | 0.051 |
| F | 1.143 | 0.071 | 1.266 | 0.063 | 0.048 | 0.058 | 1.585 | 0.060 | 1.474 | 0.792 | 0.857 | 0.084 |
| G | 1.261 | 0.504 | 0.088 | 0.086 | 0.705 | 0.083 | 1.624 | 1.709 | 0.484 | 0.055 | 0.792 | 0.073 |
| H | 0.048 | 0.057 | 0.053 | 0.063 | 0.048 | 0.082 | 0.082 | 0.101 | 0.050 | 0.060 | 0.048 | 0.053 |

Plate 2 OD450

| | 1 | 2 | 3 | 4 | 5 | 6 | 7 | 8 | 9 | 10 | 11 | 12 |
|---|---|---|---|---|---|---|---|---|---|---|---|---|
| A | 0.067 | 0.233 | 0.834 | 0.054 | 0.052 | 0.049 | 1.304 | 0.316 | 0.818 | 0.065 | 0.679 | 0.085 |
| B | 0.055 | 0.047 | 0.563 | 0.044 | 0.044 | 0.043 | 0.056 | 0.125 | 0.051 | 0.049 | 0.306 | 1.712 |
| C | 0.049 | 0.048 | 1.511 | 0.044 | 0.043 | 0.044 | 0.050 | 0.066 | 0.110 | 0.055 | 0.305 | 0.947 |
| D | 0.047 | 0.049 | 0.921 | 0.045 | 0.044 | 0.046 | 0.162 | 0.748 | 0.096 | 0.718 | 1.044 | 1.864 |
| E | 0.054 | 0.052 | 0.049 | 0.044 | 0.046 | 0.044 | 0.927 | 0.520 | 0.046 | 0.052 | 1.127 | 0.055 |
| F | 0.048 | 0.282 | 0.053 | 0.044 | 0.043 | 0.045 | 0.399 | 0.057 | 0.050 | 0.604 | 0.718 | 0.056 |
| G | 0.059 | 0.048 | 0.046 | 0.044 | 0.087 | 0.046 | 0.410 | 0.051 | 0.347 | 0.050 | 0.249 | 0.055 |
| H | 0.096 | 0.060 | 0.055 | 0.051 | 0.047 | 0.044 | 0.049 | 0.051 | 0.052 | 0.049 | 0.056 | 0.063 |

Figure 7

| | 4/20/16 ELISA | 4/14/16 FACS | Previous dose response FACS |
|---|---|---|---|
| E1-3B4 | ++++ | + | YES |
| E1-3E5 | ++++ | ++++ | YES |
| E1-3E9 | +++ | ++ | YES |
| E1-3F6 | ++++/++ | + | YES |
| E1-3H7 | ++++/+ | ++++ | YES |
| E5-3B2 | ++++/+ | ++++ | YES |
| ET1-3B1 | +++/+ | +++ | YES |
| ET1-3D6 | +++ | ++ | |
| ET1-3E12 | ++ | ++ | YES |
| P1-2A11 | ++++/++ | ++++ | YES |
| P2-2D12 | ++++ | ++++ | YES |
| P4-2F1 | +++ | ++ | |
| T1-3G7 | +++ | + | |
| TT1-3C6 | +++/++ | ++++ | YES |
| TT1-3C8 | +++/+ | ++++ | YES |
| TT1-3F5 | ++++/+++ | ++++ | YES |
| TT5-3E2 | +++ | ++ | YES |

Figure 8. Anti-GITR mAb binding to the GITR(+) CHO cell lines were tested by 5-point 2X serial dilutions in duplicates. Each mAb starting concentration was 1.5ug/ml except that ET1-3F5 started 1 ug/ml & TT1-3C6 started at 0.75 ug/ml. Note that the highest concentration of each mAb showed no binding to GITR(-) control cells (data not shown).

Anti-GITR mAb binding to the GITR(+) CHO cell lines were tested by 5-point 2X serial dilutions in duplicates. Each mAb starting concentration was 1.5ug/ml except that ET1-3F5 started 0.5 ug/ml, TT1-3C6 and TT1-3C8 started at 0.75ug/ml. Note that the highest concentration of each mAb showed no binding to GITR(-) control cells (data not shown).

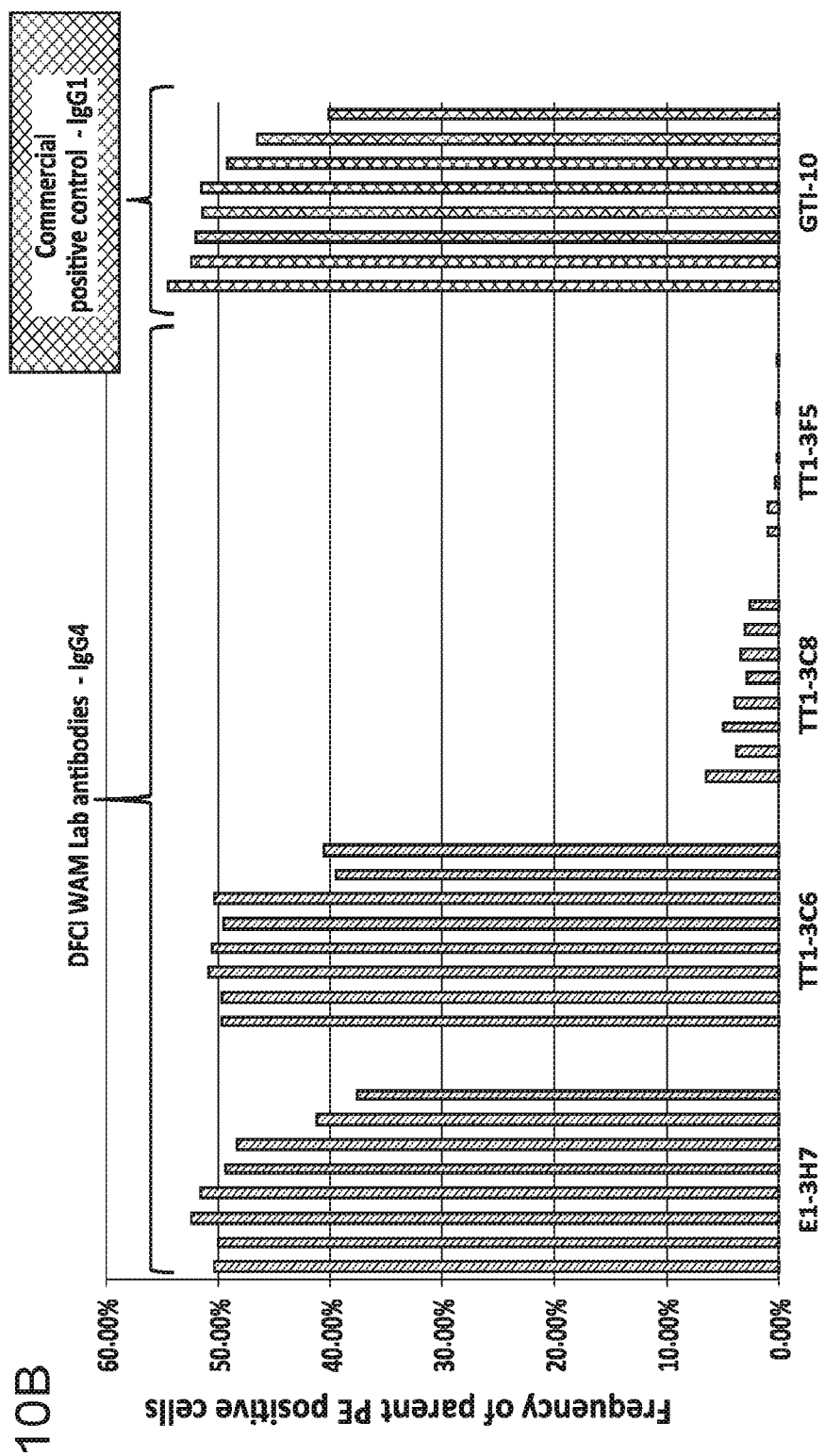

SEQUENCE LISTING

```
<160> NUMBER OF SEQ ID NOS: 122

<210> SEQ ID NO 1
<211> LENGTH: 364
<212> TYPE: DNA
<213> ORGANISM: Homo sapiens

<400> SEQUENCE: 1
caggtgcagc tggtgcagtc tgggggaggc gtggtacagc ctggggggtc cctgagactc      60
tcctgtgcag cctctggatt cacctttgat gattatgcca tgcactgggt ccggcaagct     120
ccagggaagg gcctggagtg ggtctcaagt cttagttgga atactggtcg agtagcctat     180
gcggactctg tgaagggccg attcaccatc tccagagaca acgccaagaa ttccctgtat     240
ctgcaaatga acagtctgag acctgaggac acggccttct attactgtgc aaaaggctcc     300
gcccttggct tagttggctg gttcgacgcc tggggccagg gcaccctggt caccgtctcc     360
tcag                                                                  364

<210> SEQ ID NO 2
<211> LENGTH: 121
<212> TYPE: PRT
<213> ORGANISM: Homo sapiens

<400> SEQUENCE: 2

Gln Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30
```

Ala Met His Trp Val Arg Gln Ala Pro Gly Lys Gly Leu Glu Trp Val
            35                  40                  45

Ser Ser Leu Ser Trp Asn Thr Gly Arg Val Ala Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Pro Glu Asp Thr Ala Phe Tyr Tyr Cys
                 85                  90                  95

Ala Lys Gly Ser Ala Leu Gly Leu Val Gly Trp Phe Asp Ala Trp Gly
            100                 105                 110

Gln Gly Thr Leu Val Thr Val Ser Ser
            115                 120

<210> SEQ ID NO 3
<211> LENGTH: 322
<212> TYPE: DNA
<213> ORGANISM: Homo sapiens

<400> SEQUENCE: 3
tcttctgagc tgactcagga ccctgctgtg tctgtggcct tgggacagac agtcaggatc        60
acatgccaag agacagtct cagaacctat tatggaagtt ggtaccagca aaagccagga       120 caggccccctc tacttgtctt ctatggcaaa gagagtcggc cctcagggat cccagaccga      180
ttctctggct ccacctcagg aaacacagct tccttgacca tcactgggc tcaggcggaa       240 gatgaggctg actattactg taactcccag gacagcagtg gtgacttatt attcggcgga      300
gggaccaagc tgaccgtcct ag                                              322

<210> SEQ ID NO 4
<211> LENGTH: 107
<212> TYPE: PRT
<213> ORGANISM: Homo sapiens

<400> SEQUENCE: 4

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Tyr Tyr Gly
            20                  25                  30

Ser Trp Tyr Gln Gln Lys Pro Gly Gln Ala Pro Leu Leu Val Phe Tyr
            35                  40                  45

Gly Lys Glu Ser Arg Pro Ser Gly Ile Pro Asp Arg Phe Ser Gly Ser
 50                  55                  60

Thr Ser Gly Asn Thr Ala Ser Leu Thr Ile Thr Gly Ala Gln Ala Glu
 65                  70                  75                  80

Asp Glu Ala Asp Tyr Tyr Cys Asn Ser Gln Asp Ser Ser Gly Asp Leu
                 85                  90                  95

Leu Phe Gly Gly Gly Thr Lys Leu Thr Val Leu
            100                 105

<210> SEQ ID NO 5
<211> LENGTH: 352
<212> TYPE: DNA
<213> ORGANISM: Homo sapiens

<400> SEQUENCE: 5
caggtgcagc tggtgcaatc tgggggaggc ttggtccagt ctggggaagtc cgtgagactc        60 tcttgtgcag cctctggatt cacatttggt gattatgcca tgcactgggt ccggcaagct       120

-continued

```
ccaggaaagg gcctggagtg ggtcgcaggc attactagga atagtggtcg catagcctat      180
gcggactttg tgaagggccg attcatcatc tccagagaca acgccaagaa ctcactgtat      240
ctgcaaatga acagcctgag agccgaggac acggctgtgt attactgtgc gagcgaaatg      300
actggggctt atgatatttg gggccaaggg accacggtca ccgtctcctc ag             352
```

<210> SEQ ID NO 6
<211> LENGTH: 117
<212> TYPE: PRT
<213> ORGANISM: Homo sapiens

<400> SEQUENCE: 6

```
Gln Val Gln Leu Val Gln Ser Gly Gly Gly Leu Val Gln Ser Gly Lys
1               5                   10                  15

Ser Val Arg Leu Ser Cys Ala Ala Ser Gly Phe Thr Phe Gly Asp Tyr
            20                  25                  30

Ala Met His Trp Val Arg Gln Ala Pro Gly Lys Gly Leu Glu Trp Val
        35                  40                  45

Ala Gly Ile Thr Arg Asn Ser Gly Arg Ile Ala Tyr Ala Asp Phe Val
    50                  55                  60

Lys Gly Arg Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Glu Met Thr Gly Ala Tyr Asp Ile Trp Gly Gln Gly Thr Thr
            100                 105                 110

Val Thr Val Ser Ser
        115
```

<210> SEQ ID NO 7
<211> LENGTH: 325
<212> TYPE: DNA
<213> ORGANISM: Homo sapiens

<400> SEQUENCE: 7

```
tcttctgagc tgactcagga ccctgctgtg tctgtggcct tgggacagac agtcaggatc      60
acatgccaag gagacggcct cagatactat tatgcaagct ggtaccagca gaagccagga      120
caggccccta tacttgtcct ctttggtaaa aacaaccggc cctcagggat cccagaccga      180
ttctctggct ccagctcagg aaatacagct tccttgacca tcactggggc tcaggcggaa      240
gatgaggctg actattactg taactcgcgg gacagcagtg gtaaccatcg attcttcgga      300
actgggacca aggtcaccgt cctaa                                            325
```

<210> SEQ ID NO 8
<211> LENGTH: 108
<212> TYPE: PRT
<213> ORGANISM: Homo sapiens

<400> SEQUENCE: 8

```
Ser Ser Glu Leu Thr Gln Asp Pro Ala Val Ser Val Ala Leu Gly Gln
1               5                   10                  15

Thr Val Arg Ile Thr Cys Gln Gly Asp Gly Leu Arg Tyr Tyr Tyr Ala
            20                  25                  30

Ser Trp Tyr Gln Gln Lys Pro Gly Gln Ala Pro Ile Leu Val Leu Phe
        35                  40                  45

Gly Lys Asn Asn Arg Pro Ser Gly Ile Pro Asp Arg Phe Ser Gly Ser
    50                  55                  60
```

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Arg Phe Phe Gly Thr Gly Thr Lys Val Thr Val Leu
            100                 105

<210> SEQ ID NO 9
<211> LENGTH: 361
<212> TYPE: DNA
<213> ORGANISM: Homo sapiens

<400> SEQUENCE: 9
caggtgcagc tggtgcagtc tggggggaggc gtggtccagc ctgggaggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtat attactgtgc gaaagaggat     300
tactatgata gtagtggttc gaactactgg ggccagggaa ccctggtcac cgtctcctca     360
g                                                                     361

<210> SEQ ID NO 10
<211> LENGTH: 120
<212> TYPE: PRT
<213> ORGANISM: Homo sapiens

<400> SEQUENCE: 10

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asp Tyr Tyr Asp Ser Ser Gly Ser Asn Tyr Trp Gly Gln
            100                 105                 110

Gly Thr Leu Val Thr Val Ser Ser
        115                 120

<210> SEQ ID NO 11
<211> LENGTH: 331
<212> TYPE: DNA
<213> ORGANISM: Homo sapiens

<400> SEQUENCE: 11
ctgcctgtgc tgactcagcc accctcagcg tctgggaccc ccgggcagag ggtcaccatc      60
tcttgttctg gaagcagctc caacatcgga agtaattatg tatactggta ccagcagctc     120
ccaggaacgg cccccaaact cctcacctat aggaatgatc agcggccctc aggggtccct     180
gaccgattct ctggctccaa gtctggcacc tcagcctccc tggccatcag tgggctccgg     240

```
tccgaggatg aggctgatta tttctgttca gcttgggatg acagcctggg tggcgaggtc    300
ttcggaactg ggaccaaggt caacgtccta g                                   331
```

<210> SEQ ID NO 12
<211> LENGTH: 110
<212> TYPE: PRT
<213> ORGANISM: Homo sapiens

<400> SEQUENCE: 12

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Thr Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Phe Cys Ser Ala Trp Asp Asp Ser Leu
                85                  90                  95

Gly Gly Glu Val Phe Gly Thr Gly Thr Lys Val Asn Val Leu
            100                 105                 110
```

<210> SEQ ID NO 13
<211> LENGTH: 355
<212> TYPE: DNA
<213> ORGANISM: Homo sapiens

<400> SEQUENCE: 13

```
caggtgcagc tggtgcagtc tgggggaggc ttggtacagc ctggggggtc cctgagactc    60
tcctgtgcag cctctggatt caccttagc agccatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaatcggt    300
acggcggatg cttttgatat ctggggccaa gggaccacgg tcaccgtctc ctcag         355
```

<210> SEQ ID NO 14
<211> LENGTH: 118
<212> TYPE: PRT
<213> ORGANISM: Homo sapiens

<400> SEQUENCE: 14

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Ile Gly Thr Ala Asp Ala Phe Asp Ile Trp Gly Gln Gly Thr
            100                 105                 110

Thr Val Thr Val Ser Ser
        115

<210> SEQ ID NO 15
<211> LENGTH: 331
<212> TYPE: DNA
<213> ORGANISM: Homo sapiens

<400> SEQUENCE: 15

```
cagtctgccc tgactcagcc accctcagtg tctgggaccc ccggacagag ggtcaccatc    60
tcttgttctg gaggcgtccc caacatcgga agtaatcctg taaactggta cctccaccgc   120
ccaggaacgg cccccaaact cctcatctat aatagcaatc agtggcctc aggggtccct    180 gaccgatttt ctggctccag gtctggcacc tcagcctccc tggccatcag tgggctccag   240
tctgaggatg aggctgatta ttactgtgca gcatgggatg acagcctgga tggtctggtt   300
ttcggcggag ggaccaagtt gaccgtccta g                                  331
```

<210> SEQ ID NO 16
<211> LENGTH: 110
<212> TYPE: PRT
<213> ORGANISM: Homo sapiens

<400> SEQUENCE: 16

Gln Ser Ala Leu Thr Gln Pro Pro Ser Val Ser Gly Thr Pro Gly Gln
1               5                   10                  15

Arg Val Thr Ile Ser Cys Ser Gly Gly Val Pro Asn Ile Gly Ser Asn
            20                  25                  30

Pro Val Asn Trp Tyr Leu His Arg Pro Gly Thr Ala Pro Lys Leu Leu
        35                  40                  45

Ile Tyr Asn Ser Asn Gln Trp Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly Leu Val Phe Gly Gly Gly Thr Lys Leu Thr Val Leu
            100                 105                 110

<210> SEQ ID NO 17
<211> LENGTH: 373
<212> TYPE: DNA
<213> ORGANISM: Homo sapiens

<400> SEQUENCE: 17

```
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaaccta gtggtggtag cacaagctac     180
gcacagaagt tccagggcag agtcaccatg accagggaca cgtccacgag cacagtctac   240
atggagctga gcagcctgag atctgaggac acggccgtgt attactgtgc tagagaaaaa   300
agcagcagct ggtacggggg ggacaactgg ttcgacccct ggggccaggg caccctggtc   360
accgtctcct cag                                                      373
```

<210> SEQ ID NO 18
<211> LENGTH: 124
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Lys Ser Ser Ser Trp Tyr Gly Gly Asp Asn Trp Phe Asp
            100                 105                 110

Pro Trp Gly Gln Gly Thr Leu Val Thr Val Ser Ser
        115                 120

<210> SEQ ID NO 19
<211> LENGTH: 331
<212> TYPE: DNA
<213> ORGANISM: Homo sapiens

<400> SEQUENCE: 19
cagtctgccc tgactcagcc tcgctcagtg tccgggtctc ctggacagtc agtcaccatc      60
tcctgcactg gaagcagcag tgatgttggt ggttatcatt atgtctcctg gtaccaacaa     120
tacccaggca aagtccccaa actgatgatt tatgatgtct ctaggcggcc ctcaggggtt     180
tctgatcgct tctctggctc caagtctggc agcacggcct ccctgaccat ctctgggctc     240
caggctgagg acgaggctga ttattactgc agctcatata caagcagcag cactgtggtc     300
ttcggcggag ggaccaagct gaccgtccta c                                    331

<210> SEQ ID NO 20
<211> LENGTH: 110
<212> TYPE: PRT
<213> ORGANISM: Homo sapiens

<400> SEQUENCE: 20

Gln Ser Ala Leu Thr Gln Pro Arg Ser Val Ser Gly Ser Pro Gly Gln
1               5                   10                  15

Ser Val Thr Ile Ser Cys Thr Gly Ser Ser Ser Asp Val Gly Gly Tyr
            20                  25                  30

His Tyr Val Ser Trp Tyr Gln Gln Tyr Pro Gly Lys Val Pro Lys Leu
        35                  40                  45

Met Ile Tyr Asp Val Ser Arg Arg Pro Ser Gly Val Ser Asp Arg Phe
    50                  55                  60

Ser Gly Ser Lys Ser Gly Ser Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110

<210> SEQ ID NO 21
<211> LENGTH: 390
<212> TYPE: DNA
<213> ORGANISM: Homo sapiens

<400> SEQUENCE: 21
caggtgcagc tggtgcaatc tggagctgag gtgaagaagc ctggggcctc agtgaaggtc    60
tcctgcaagg cttctggtta ccctttacc agctatggta tcagctgggt gcgacaggcc   120
cctggacaag gcttgagtg atgggatgg atcagcgctt acaatggtaa cacaaactat   180
gcacagaagc tccagggcag agtcaccatg accacagaca catccacgag cacagcctac   240
atggagctga ggagcctgag atctgacgac acggccgtgt attactgtgc gagagatgta   300
caccccttag atatagcagt ggctgccgac gattactact actacggtat ggacgtctgg   360
ggccaaggca ccctggtcac cgtctcctca                                    390

<210> SEQ ID NO 22
<211> LENGTH: 130
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val His Pro Leu Asp Ile Ala Val Ala Ala Asp Asp Tyr
            100                 105                 110

Tyr Tyr Tyr Gly Met Asp Val Trp Gly Gln Gly Thr Leu Val Thr Val
        115                 120                 125

Ser Ser
    130

<210> SEQ ID NO 23
<211> LENGTH: 325
<212> TYPE: DNA
<213> ORGANISM: Homo sapiens

<400> SEQUENCE: 23
tcttctgagc tgactcagga ccctgctgtg tctgtggcct tgggacagac agtcaggatc    60
acatgccaag agacagcct cacaaccaat tatgcaagct ggtaccagca gaagccagga   120
caggcccctg ttcttgtcat ctatggtaaa acaagcggc cctcagggat cccagaccga   180
ttctctggct ccatctcagg gaacacagct tccttgacca tcactggggc tcaggcggag   240
gatgaggctg actattactg taactcccgg gacagcagtg gtaagcatta tgtcttcgga   300
actgggacca aggtcaccgt cctag                                         325

<210> SEQ ID NO 24
<211> LENGTH: 108
<212> TYPE: PRT
<213> ORGANISM: Homo sapiens

<400> SEQUENCE: 24

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Thr Thr Asn Tyr Ala
            20                  25                  30

Ser Trp Tyr Gln Gln Lys Pro Gly Gln Ala Pro Val Leu Val Ile Tyr
        35                  40                  45

Gly Lys Asn Lys Arg Pro Ser Gly Ile Pro Asp Arg Phe Ser Gly Ser
    50                  55                  60

Ile Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Lys His
                85                  90                  95

Tyr Val Phe Gly Thr Gly Thr Lys Val Thr Val Leu
            100                 105
```

<210> SEQ ID NO 25
<211> LENGTH: 367
<212> TYPE: DNA
<213> ORGANISM: Homo sapiens

<400> SEQUENCE: 25

```
gaggtgcagc tggtggagtc tgggggaggc gtggtccagc ctggggaggtc cctgagactc    60
tcctgtgcag cctctggatt caccttagc agctatgcca tgagctgggt ccgccaggct    120
ccagggaagg gctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagattgg    300
ggcctagtac aactggaatc cggctatgac tactggggcc agggaaccct ggtcaccgtc    360
tcctcag                                                              367
```

<210> SEQ ID NO 26
<211> LENGTH: 122
<212> TYPE: PRT
<213> ORGANISM: Homo sapiens

<400> SEQUENCE: 26

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Trp Gly Leu Val Gln Leu Glu Ser Gly Tyr Asp Tyr Trp
            100                 105                 110
```

Gly Gln Gly Thr Leu Val Thr Val Ser Ser
            115                 120

<210> SEQ ID NO 27
<211> LENGTH: 334
<212> TYPE: DNA
<213> ORGANISM: Homo sapiens

<400> SEQUENCE: 27
cagtctgtgc tgactcagcc accctcagtg tctggggccc cagggcagag ggtcaccatc    60
tcctgcactg ggagcagctc aacatcggg gcaggttatg atgtacactg gtaccaacag   120
cttccaggaa aagcccccaa actcctcatc tatgataata ccaatcggcc ctcgggggtc   180
cctgaccgat tctctggctc caagtctggc acctcagcct ccctggccat cagtgggctc   240
cagtctgagg atgaggctga ttattactgt gcagcatggg atgaaagcct gaatggtcag   300
gtcttcggaa ctgggaccaa ggtcaccgtc ctag                              334

<210> SEQ ID NO 28
<211> LENGTH: 111
<212> TYPE: PRT
<213> ORGANISM: Homo sapiens

<400> SEQUENCE: 28

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Lys Ala Pro Lys Leu
        35                  40                  45

Leu Ile Tyr Asp Asn Thr Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Glu Ser
                85                  90                  95

Leu Asn Gly Gln Val Phe Gly Thr Gly Thr Lys Val Thr Val Leu
            100                 105                 110

<210> SEQ ID NO 29
<211> LENGTH: 367
<212> TYPE: DNA
<213> ORGANISM: Homo sapiens

<400> SEQUENCE: 29
caggtacagc tgcagcagtc aggcccagga ctggtgaagc cttcggggac cctgtccctc    60
acctgcgctg tctctggtgg ctccatcagc agtagtgact ggtggagttg ggtccgccag   120
gtcccaggga aggggctgga gtggattggg gaaatctatc acagtggcag tccaactac    180 aacccgtccc tcagggtcg agtcaccata tcagtagaca gtcgaagaa ccagttctcc    240 ctgaagctga gctctgtgac cgccgcggac acggccgtct attactgtgc gagagaaaga   300
gttgctccta cagtagacgg tgcttttgat gtctggggcc aagggacaat ggtcaccgtc   360
tcctcag                                                            367

<210> SEQ ID NO 30
<211> LENGTH: 122
<212> TYPE: PRT
<213> ORGANISM: Homo sapiens

<400> SEQUENCE: 30

Gln Val Gln Leu Gln Gln Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asp Trp Trp Ser Trp Val Arg Gln Val Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Arg Gly Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Arg Val Ala Pro Thr Val Asp Gly Ala Phe Asp Val Trp
            100                 105                 110

Gly Gln Gly Thr Met Val Thr Val Ser Ser
        115                 120

<210> SEQ ID NO 31
<211> LENGTH: 322
<212> TYPE: DNA
<213> ORGANISM: Homo sapiens

<400> SEQUENCE: 31
gacatcgtga tgacccagtc tccatcctcc ctgtctgcat ctgtaggaga cagagtcacc      60
atcacttgcc gggcaagtca gagcattacc acctatttaa attggtatca gcagaaacca    120
gggaaagccc ctaagctcct gatctatgct gcatccagtt tgcaaagtgg ggtcccatca    180
aggttcagtg gcagtggatc tgggacagaa ttcactctca ctatcagcag cctgcagcct    240
gaagattttg caacttatta ttgtcaacag gccagcagtt tccctctcac tttcggcgga    300
gggaccaagg tggatctcaa ac                                              322

<210> SEQ ID NO 32
<211> LENGTH: 107
<212> TYPE: PRT
<213> ORGANISM: Homo sapiens

<400> SEQUENCE: 32

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Ser Ser Phe Pro Leu
                85                  90                  95

Thr Phe Gly Gly Gly Thr Lys Val Asp Leu Lys
            100                 105

<210> SEQ ID NO 33
<211> LENGTH: 364

<212> TYPE: DNA
<213> ORGANISM: Homo sapiens

<400> SEQUENCE: 33

```
gaggtgcagc tggtgcagtc tggagctgag gtgaaaaagc ccggggagtc tctgaagatc    60
tcctgtaagg gttcgggata cagctttacc aactactgga tcggctgggt gcgccagatg   120
cccgggaaag gcctggagtg gattgggatc atctatcctg gtgactctga taccagatac   180
agcccgtcct tccaaggcca ggtcaccatc tcagccgaca gtccaccag cactgcctac    240
ctgcagtgga gcagcctgaa ggcctcggac accgccatgt attactgtgc gaggataaag   300
agttactatg atagtagtgg ttattacctc tggggccagg gaaccctggt caccgtctcc   360
tcag                                                                364
```

<210> SEQ ID NO 34
<211> LENGTH: 121
<212> TYPE: PRT
<213> ORGANISM: Homo sapiens

<400> SEQUENCE: 34

```
Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Asn Tyr
            20                  25                  30
Trp Ile Gly Trp Val Arg Gln Met Pro Gly Lys Gly Leu Glu Trp Ile
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Asp Lys Ser Thr Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg Ile Lys Ser Tyr Tyr Asp Ser Ser Gly Tyr Tyr Leu Trp Gly
            100                 105                 110
Gln Gly Thr Leu Val Thr Val Ser Ser
        115                 120
```

<210> SEQ ID NO 35
<211> LENGTH: 322
<212> TYPE: DNA
<213> ORGANISM: Homo sapiens

<400> SEQUENCE: 35

```
cagtctgtgc tgactcagcc accctcggtg tcagtggccc caggacagac ggccagcata    60
acctgtgggg gaaacaacat tgggagtaaa agtgtgcact ggtaccagca gaagccaggc   120
caggcccctg tcctggtcgt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtagta gtgaagaggt attcggcgga   300
gggaccaagc tgaccgtcct ag                                            322
```

<210> SEQ ID NO 36
<211> LENGTH: 107
<212> TYPE: PRT
<213> ORGANISM: Homo sapiens

<400> SEQUENCE: 36

Gln Ser Val Leu Thr Gln Pro Pro Ser Val Ser Ala Pro Gly Gln
1               5                   10                  15

Thr Ala Ser Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Glu
            85                  90                  95

Val Phe Gly Gly Gly Thr Lys Leu Thr Val Leu
            100                 105

<210> SEQ ID NO 37
<211> LENGTH: 346
<212> TYPE: DNA
<213> ORGANISM: Homo sapiens

<400> SEQUENCE: 37
gaggtgcagc tggtgcagtc tggggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgacgac acggctgtct attactgtgc gagaaggggg   300
ttcatggacg tctggggcaa aggcaccctg gtcaccgtct cctcag              346

<210> SEQ ID NO 38
<211> LENGTH: 115
<212> TYPE: PRT
<213> ORGANISM: Homo sapiens

<400> SEQUENCE: 38

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
            85                  90                  95

Ala Arg Arg Gly Phe Met Asp Val Trp Gly Lys Gly Thr Leu Val Thr
            100                 105                 110

Val Ser Ser
        115

<210> SEQ ID NO 39
<211> LENGTH: 325
<212> TYPE: DNA
<213> ORGANISM: Homo sapiens

<400> SEQUENCE: 39

```
tcttctgagc tgactcagga ccctgctgtg tctgtggcct tgggacagac agtcaccatc    60
acatgccaag agacatcct  cgaagcctat tatgcaagtt ggtaccagca gaggccagga   120
caggcccctg tccttgtcat ctatggcgaa acaaccggc  cctcagggat cccagaccgg   180
ttctctggct ccaggtcagg aaacacagcc tccttgacca tcactggggc tcaggcggaa   240
gatgaggctg actattattg taactctcgg acagcagtg  gtagccatgt ggtattcggc   300
ggagggacca agatgaccgt cctgg                                         325
```

<210> SEQ ID NO 40
<211> LENGTH: 108
<212> TYPE: PRT
<213> ORGANISM: Homo sapiens

<400> SEQUENCE: 40

```
Ser Ser Glu Leu Thr Gln Asp Pro Ala Val Ser Val Ala Leu Gly Gln
1               5                  10                  15
Thr Val Thr Ile Thr Cys Gln Gly Asp Ile Leu Glu Ala Tyr Tyr Ala
            20                  25                  30
Ser Trp Tyr Gln Gln Arg Pro Gly Gln Ala Pro Val Leu Val Ile Tyr
        35                  40                  45
Gly Glu Asn Asn Arg Pro Ser Gly Ile Pro Asp Arg Phe Ser Gly Ser
    50                  55                  60
Arg Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Ser His
                85                  90                  95
Val Val Phe Gly Gly Gly Thr Lys Met Thr Val Leu
            100                 105
```

<210> SEQ ID NO 41
<211> LENGTH: 346
<212> TYPE: DNA
<213> ORGANISM: Homo sapiens

<400> SEQUENCE: 41

```
caggtgcagc tggtgcagtc tgggggaggc ttggtacagc ctggggggtc cctgagactc    60
tcctgtgcag cctctggatt cacctttaac agctttgcca tgacctgggt ccgccaggct   120
ccagggaagg gctggagtg  ggtctcaggt attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaagggcac   300
gcttttgata tctggggcca agggaccacg gtcaccgtct cctcag                  346
```

<210> SEQ ID NO 42
<211> LENGTH: 115
<212> TYPE: PRT
<213> ORGANISM: Homo sapiens

<400> SEQUENCE: 42

```
Gln Val Gln Leu Val Gln Ser Gly Gly Gly Leu Val Gln Pro Gly Gly
1               5                  10                  15
Ser Leu Arg Leu Ser Cys Ala Ala Ser Gly Phe Thr Phe Asn Ser Phe
            20                  25                  30
Ala Met Thr Trp Val Arg Gln Ala Pro Gly Lys Gly Leu Glu Trp Val
        35                  40                  45
```

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Ala Phe Asp Ile Trp Gly Gln Gly Thr Thr Val Thr
            100                 105                 110

Val Ser Ser
        115

<210> SEQ ID NO 43
<211> LENGTH: 337
<212> TYPE: DNA
<213> ORGANISM: Homo sapiens

<400> SEQUENCE: 43
gacatcgtga tgacccagtc tccactctct ctgtccgtca cccctgggca gccggcctcc      60
atctcctgca gtctagtca gagcctcctg catagtgatg gaaagaccta tttgtattgg     120
tacctgcaga agccaggcca gcctccacaa ctcctgatct atgaagtttc caaccggttc     180
tctggagtgc cagataggtt cagtggcagc gggtcaggga cagatttcac actgaaaatc     240
agccgggtgg aggctgagga tgttggggtt tattactgca tgcaaagtat acagcttcct     300
ctcactttcg gcggagggac caaggtggag atcaaac                             337

<210> SEQ ID NO 44
<211> LENGTH: 112
<212> TYPE: PRT
<213> ORGANISM: Homo sapiens

<400> SEQUENCE: 44

Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
            100                 105                 110

<210> SEQ ID NO 45
<211> LENGTH: 352
<212> TYPE: DNA
<213> ORGANISM: Homo sapiens

<400> SEQUENCE: 45
caggtgcagc tggtgcagtc tggggaggc ttggtacagc ctgggggtc cctgagactc       60 tcctgtgcag cctctggatt cacctttagc agctatgcca tgagctgggt ccgccaggct    120
ccagggaagg ggctggagtg ggtctcagct attagtggta gtggtggtag cacatactac    180

```
gcagactccg tgaagggccg gttcaccatc tccagagaca attccaagaa cacgctgtat    240
ctgcaaatga acagcctgag agccgaggac acggctgtgt attactgtgc gaaagataaa   300
ggtggggggt cgacccctg gggccaggga accctggtca ccgtctcctc ag           352
```

<210> SEQ ID NO 46
<211> LENGTH: 117
<212> TYPE: PRT
<213> ORGANISM: Homo sapiens

<400> SEQUENCE: 46

```
Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Gly Gly Gly Phe Asp Pro Trp Gly Gln Gly Thr Leu
            100                 105                 110

Val Thr Val Ser Ser
        115
```

<210> SEQ ID NO 47
<211> LENGTH: 331
<212> TYPE: DNA
<213> ORGANISM: Homo sapiens

<400> SEQUENCE: 47

```
aattttatgc tgactcagcc ccactctgtg tcggagtctc cggggaagac ggtaaccatc    60
tcctgcaccc gcagcagtgg cagcattgcc agcaactatg tgcagtggta ccagcagcgc   120
ccgggcagtt cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgatagtac ctctcatgtc   300
ttcggaactg ggacccaggt caccgtccta g                                 331
```

<210> SEQ ID NO 48
<211> LENGTH: 110
<212> TYPE: PRT
<213> ORGANISM: Homo sapiens

<400> SEQUENCE: 48

```
Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
```

```
                65                  70                  75                  80
Leu Lys Thr Glu Asp Glu Ala Asp Tyr Tyr Cys Gln Ser Tyr Asp Ser
                    85                  90                  95

Thr Ser His Val Phe Gly Thr Gly Thr Gln Val Thr Val Leu
                100                 105                 110

<210> SEQ ID NO 49
<211> LENGTH: 373
<212> TYPE: DNA
<213> ORGANISM: Homo sapiens

<400> SEQUENCE: 49
gaggtgcagc tggtgcagtc tggagcagag gtgaaaaagc ccggggagtc tctgaagatc    60
tcctgtaagg gttctggata cagctttacc aactactgga tcggctgggt gcgccagatg   120
cccgggaaag gcctggagtg ggtggggatc atctatcctg gtgactctga taccagatac   180
agcccgtcct tccaaggcca ggtcaccatc tcagccgaca gtccatcagc accgcctac    240 ctgcagtgga gcagcctgaa ggcctcggac accgccatgt attactgtgc agaaccaggg   300
tattactatg gttcggggag ttattataac gttgactact ggggccaggg caccctggtc   360
accgtctcct cag                                                      373

<210> SEQ ID NO 50
<211> LENGTH: 124
<212> TYPE: PRT
<213> ORGANISM: Homo sapiens

<400> SEQUENCE: 50

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Val
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Pro Gly Tyr Tyr Tyr Gly Ser Gly Ser Tyr Tyr Asn Val Asp
                100                 105                 110

Tyr Trp Gly Gln Gly Thr Leu Val Thr Val Ser Ser
            115                 120

<210> SEQ ID NO 51
<211> LENGTH: 322
<212> TYPE: DNA
<213> ORGANISM: Homo sapiens

<400> SEQUENCE: 51
cagcctgggc tgactcagcc accctcagtg tccgtgtccc caggacagac agccagcatc    60
acctgctctg gagatgaatt gggggataaa tttgctttct ggtatcaaca aaagccaggc   120
cagtcccctg tgctggtcat ctatcaagat agtaagaggc cctcagggat ccctgagcga   180
ttctctggct ccatctctgg gaacacggcc accctgacta tcagcagggt cgaggccgga   240
gatgaggccg actatttctg tcaggtgtgg gatagcaatg gtggtccccc attcggagga   300
```
gggaccaagc tgaccgtcct ag                                          322

<210> SEQ ID NO 52
<211> LENGTH: 107
<212> TYPE: PRT
<213> ORGANISM: Homo sapiens

<400> SEQUENCE: 52

Gln Pro Gly Leu Thr Gln Pro Pro Ser Val Ser Val Ser Pro Gly Gln
1               5                   10                  15

Thr Ala Ser Ile Thr Cys Ser Gly Asp Glu Leu Gly Asp Lys Phe Ala
            20                  25                  30

Phe Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Ile Ser Gly Asn Thr Ala Thr Leu Thr Ile Ser Arg Val Glu Ala Gly
65                  70                  75                  80

Asp Glu Ala Asp Tyr Phe Cys Gln Val Trp Asp Ser Asn Gly Pro Pro
                85                  90                  95

Pro Phe Gly Arg Gly Thr Lys Leu Thr Val Leu
            100                 105

<210> SEQ ID NO 53
<211> LENGTH: 8
<212> TYPE: PRT
<213> ORGANISM: Homo sapiens

<400> SEQUENCE: 53

Gly Phe Thr Phe Asp Asp Tyr Ala
1               5

<210> SEQ ID NO 54
<211> LENGTH: 8
<212> TYPE: PRT
<213> ORGANISM: Homo sapiens

<400> SEQUENCE: 54

Leu Ser Trp Asn Thr Gly Arg Val
1               5

<210> SEQ ID NO 55
<211> LENGTH: 14
<212> TYPE: PRT
<213> ORGANISM: Homo sapiens

<400> SEQUENCE: 55

Ala Lys Gly Ser Ala Leu Gly Leu Val Gly Trp Phe Asp Ala
1               5                   10

<210> SEQ ID NO 56
<211> LENGTH: 6
<212> TYPE: PRT
<213> ORGANISM: Homo sapiens

<400> SEQUENCE: 56

Ser Leu Arg Thr Tyr Tyr
1               5

<210> SEQ ID NO 57
<211> LENGTH: 3

<212> TYPE: PRT
<213> ORGANISM: Homo sapiens

<400> SEQUENCE: 57

Gly Lys Glu
1

<210> SEQ ID NO 58
<211> LENGTH: 10
<212> TYPE: PRT
<213> ORGANISM: Homo sapiens

<400> SEQUENCE: 58

Asn Ser Gln Asp Ser Ser Gly Asp Leu Leu
1               5                   10

<210> SEQ ID NO 59
<211> LENGTH: 8
<212> TYPE: PRT
<213> ORGANISM: Homo sapiens

<400> SEQUENCE: 59

Gly Phe Thr Phe Gly Asp Tyr Ala
1               5

<210> SEQ ID NO 60
<211> LENGTH: 8
<212> TYPE: PRT
<213> ORGANISM: Homo sapiens

<400> SEQUENCE: 60

Ile Thr Arg Asn Ser Gly Arg Ile
1               5

<210> SEQ ID NO 61
<211> LENGTH: 10
<212> TYPE: PRT
<213> ORGANISM: Homo sapiens

<400> SEQUENCE: 61

Ala Ser Glu Met Thr Gly Ala Tyr Asp Ile
1               5                   10

<210> SEQ ID NO 62
<211> LENGTH: 6
<212> TYPE: PRT
<213> ORGANISM: Homo sapiens

<400> SEQUENCE: 62

Gly Leu Arg Tyr Tyr Tyr
1               5

<210> SEQ ID NO 63
<211> LENGTH: 3
<212> TYPE: PRT
<213> ORGANISM: Homo sapiens

<400> SEQUENCE: 63

Gly Lys Asn
1

<210> SEQ ID NO 64
<211> LENGTH: 11
<212> TYPE: PRT
<213> ORGANISM: Homo sapiens

<400> SEQUENCE: 64

Asn Ser Arg Asp Ser Ser Gly Asn His Arg Phe
1               5                   10

<210> SEQ ID NO 65
<211> LENGTH: 8
<212> TYPE: PRT
<213> ORGANISM: Homo sapiens

<400> SEQUENCE: 65

Gly Phe Thr Phe Ser Ser Tyr Ala
1               5

<210> SEQ ID NO 66
<211> LENGTH: 8
<212> TYPE: PRT
<213> ORGANISM: Homo sapiens

<400> SEQUENCE: 66

Ile Ser Tyr Asp Gly Ser Asn Lys
1               5

<210> SEQ ID NO 67
<211> LENGTH: 13
<212> TYPE: PRT
<213> ORGANISM: Homo sapiens

<400> SEQUENCE: 67

Ala Lys Glu Asp Tyr Tyr Asp Ser Ser Gly Ser Asn Tyr
1               5                   10

<210> SEQ ID NO 68
<211> LENGTH: 8
<212> TYPE: PRT
<213> ORGANISM: Homo sapiens

<400> SEQUENCE: 68

Ser Ser Asn Ile Gly Ser Asn Tyr
1               5

<210> SEQ ID NO 69
<211> LENGTH: 3
<212> TYPE: PRT
<213> ORGANISM: Homo sapiens

<400> SEQUENCE: 69

Arg Asn Asp
1

<210> SEQ ID NO 70
<211> LENGTH: 11
<212> TYPE: PRT
<213> ORGANISM: Homo sapiens

<400> SEQUENCE: 70

Ser Ala Trp Asp Asp Ser Leu Gly Gly Glu Val
1               5                   10

<210> SEQ ID NO 71
<211> LENGTH: 8
<212> TYPE: PRT
<213> ORGANISM: Homo sapiens

<400> SEQUENCE: 71

Gly Phe Thr Phe Ser Ser His Ala
1               5

<210> SEQ ID NO 72
<211> LENGTH: 8
<212> TYPE: PRT
<213> ORGANISM: Homo sapiens

<400> SEQUENCE: 72

Ile Ser Gly Ser Gly Gly Ser Thr
1               5

<210> SEQ ID NO 73
<211> LENGTH: 11
<212> TYPE: PRT
<213> ORGANISM: Homo sapiens

<400> SEQUENCE: 73

Ala Lys Ile Gly Thr Ala Asp Ala Phe Asp Ile
1               5                   10

<210> SEQ ID NO 74
<211> LENGTH: 8
<212> TYPE: PRT
<213> ORGANISM: Homo sapiens

<400> SEQUENCE: 74

Val Pro Asn Ile Gly Ser Asn Pro
1               5

<210> SEQ ID NO 75
<211> LENGTH: 3
<212> TYPE: PRT
<213> ORGANISM: Homo sapiens

<400> SEQUENCE: 75

Asn Ser Asn
1

<210> SEQ ID NO 76
<211> LENGTH: 11
<212> TYPE: PRT
<213> ORGANISM: Homo sapiens

<400> SEQUENCE: 76

Ala Ala Trp Asp Asp Ser Leu Asp Gly Leu Val
1               5                   10

<210> SEQ ID NO 77
<211> LENGTH: 8
<212> TYPE: PRT
<213> ORGANISM: Homo sapiens

<400> SEQUENCE: 77

Gly Tyr Thr Phe Thr Ser Tyr Tyr
1               5

<210> SEQ ID NO 78
<211> LENGTH: 8
<212> TYPE: PRT
<213> ORGANISM: Homo sapiens

<400> SEQUENCE: 78

Ile Asn Pro Ser Gly Gly Ser Thr

```
<210> SEQ ID NO 79
<211> LENGTH: 17
<212> TYPE: PRT
<213> ORGANISM: Homo sapiens

<400> SEQUENCE: 79

Ala Arg Glu Lys Ser Ser Ser Trp Tyr Gly Gly Asp Asn Trp Phe Asp
1               5                   10                  15
Pro

<210> SEQ ID NO 80
<211> LENGTH: 9
<212> TYPE: PRT
<213> ORGANISM: Homo sapiens

<400> SEQUENCE: 80

Ser Ser Asp Val Gly Gly Tyr His Tyr
1               5

<210> SEQ ID NO 81
<211> LENGTH: 3
<212> TYPE: PRT
<213> ORGANISM: Homo sapiens

<400> SEQUENCE: 81

Asp Val Ser
1

<210> SEQ ID NO 82
<211> LENGTH: 10
<212> TYPE: PRT
<213> ORGANISM: Homo sapiens

<400> SEQUENCE: 82

Ser Ser Tyr Thr Ser Ser Ser Thr Val Val
1               5                   10

<210> SEQ ID NO 83
<211> LENGTH: 8
<212> TYPE: PRT
<213> ORGANISM: Homo sapiens

<400> SEQUENCE: 83

Gly Tyr Thr Phe Thr Ser Tyr Gly
1               5

<210> SEQ ID NO 84
<211> LENGTH: 8
<212> TYPE: PRT
<213> ORGANISM: Homo sapiens

<400> SEQUENCE: 84

Ile Ser Ala Tyr Asn Gly Asn Thr
1               5

<210> SEQ ID NO 85
<211> LENGTH: 23
<212> TYPE: PRT
<213> ORGANISM: Homo sapiens

<400> SEQUENCE: 85

Ala Arg Asp Val His Pro Leu Asp Ile Ala Val Ala Ala Asp Asp Tyr
```

```
                1               5                  10                  15

Tyr Tyr Tyr Gly Met Asp Val
                20

<210> SEQ ID NO 86
<211> LENGTH: 6
<212> TYPE: PRT
<213> ORGANISM: Homo sapiens

<400> SEQUENCE: 86

Ser Leu Thr Thr Asn Tyr
1               5

<210> SEQ ID NO 87
<211> LENGTH: 3
<212> TYPE: PRT
<213> ORGANISM: Homo sapiens

<400> SEQUENCE: 87

Gly Lys Asn
1

<210> SEQ ID NO 88
<211> LENGTH: 11
<212> TYPE: PRT
<213> ORGANISM: Homo sapiens

<400> SEQUENCE: 88

Asn Ser Arg Asp Ser Ser Gly Lys His Tyr Val
1               5                   10

<210> SEQ ID NO 89
<211> LENGTH: 15
<212> TYPE: PRT
<213> ORGANISM: Homo sapiens

<400> SEQUENCE: 89

Ala Lys Asp Trp Gly Leu Val Gln Leu Glu Ser Gly Tyr Asp Tyr
1               5                   10                  15

<210> SEQ ID NO 90
<211> LENGTH: 9
<212> TYPE: PRT
<213> ORGANISM: Homo sapiens

<400> SEQUENCE: 90

Ser Ser Asn Ile Gly Ala Gly Tyr Asp
1               5

<210> SEQ ID NO 91
<211> LENGTH: 3
<212> TYPE: PRT
<213> ORGANISM: Homo sapiens

<400> SEQUENCE: 91

Asp Asn Thr
1

<210> SEQ ID NO 92
<211> LENGTH: 11
<212> TYPE: PRT
<213> ORGANISM: Homo sapiens

<400> SEQUENCE: 92
```

Ala Ala Trp Asp Glu Ser Leu Asn Gly Gln Val
1               5                   10

<210> SEQ ID NO 93
<211> LENGTH: 9
<212> TYPE: PRT
<213> ORGANISM: Homo sapiens

<400> SEQUENCE: 93

Gly Gly Ser Ile Ser Ser Ser Asp Trp
1               5

<210> SEQ ID NO 94
<211> LENGTH: 7
<212> TYPE: PRT
<213> ORGANISM: Homo sapiens

<400> SEQUENCE: 94

Ile Tyr His Ser Gly Ser Pro
1               5

<210> SEQ ID NO 95
<211> LENGTH: 15
<212> TYPE: PRT
<213> ORGANISM: Homo sapiens

<400> SEQUENCE: 95

Ala Arg Glu Arg Val Ala Pro Thr Val Asp Gly Ala Phe Asp Val
1               5                   10                  15

<210> SEQ ID NO 96
<211> LENGTH: 6
<212> TYPE: PRT
<213> ORGANISM: Homo sapiens

<400> SEQUENCE: 96

Gln Ser Ile Thr Thr Tyr
1               5

<210> SEQ ID NO 97
<211> LENGTH: 3
<212> TYPE: PRT
<213> ORGANISM: Homo sapiens

<400> SEQUENCE: 97

Ala Ala Ser
1

<210> SEQ ID NO 98
<211> LENGTH: 9
<212> TYPE: PRT
<213> ORGANISM: Homo sapiens

<400> SEQUENCE: 98

Gln Gln Ala Ser Ser Phe Pro Leu Thr
1               5

<210> SEQ ID NO 99
<211> LENGTH: 8
<212> TYPE: PRT
<213> ORGANISM: Homo sapiens

<400> SEQUENCE: 99

Gly Tyr Ser Phe Thr Asn Tyr Trp
1               5

```
<210> SEQ ID NO 100
<211> LENGTH: 8
<212> TYPE: PRT
<213> ORGANISM: Homo sapiens

<400> SEQUENCE: 100

Ile Tyr Pro Gly Asp Ser Asp Thr
1               5

<210> SEQ ID NO 101
<211> LENGTH: 14
<212> TYPE: PRT
<213> ORGANISM: Homo sapiens

<400> SEQUENCE: 101

Ala Arg Ile Lys Ser Tyr Tyr Asp Ser Ser Gly Tyr Tyr Leu
1               5                   10

<210> SEQ ID NO 102
<211> LENGTH: 6
<212> TYPE: PRT
<213> ORGANISM: Homo sapiens

<400> SEQUENCE: 102

Asn Ile Gly Ser Lys Ser
1               5

<210> SEQ ID NO 103
<211> LENGTH: 3
<212> TYPE: PRT
<213> ORGANISM: Homo sapiens

<400> SEQUENCE: 103

Asp Asp Ser
1

<210> SEQ ID NO 104
<211> LENGTH: 10
<212> TYPE: PRT
<213> ORGANISM: Homo sapiens

<400> SEQUENCE: 104

Gln Val Trp Asp Ser Ser Ser Glu Glu Val
1               5                   10

<210> SEQ ID NO 105
<211> LENGTH: 8
<212> TYPE: PRT
<213> ORGANISM: Homo sapiens

<400> SEQUENCE: 105

Ala Arg Arg Gly Phe Met Asp Val
1               5

<210> SEQ ID NO 106
<211> LENGTH: 6
<212> TYPE: PRT
<213> ORGANISM: Homo sapiens

<400> SEQUENCE: 106

Ile Leu Glu Ala Tyr Tyr
1               5
```

```
<210> SEQ ID NO 107
<211> LENGTH: 3
<212> TYPE: PRT
<213> ORGANISM: Homo sapiens

<400> SEQUENCE: 107

Gly Glu Asn
1

<210> SEQ ID NO 108
<211> LENGTH: 11
<212> TYPE: PRT
<213> ORGANISM: Homo sapiens

<400> SEQUENCE: 108

Asn Ser Arg Asp Ser Ser Gly Ser His Val Val
1               5                   10

<210> SEQ ID NO 109
<211> LENGTH: 8
<212> TYPE: PRT
<213> ORGANISM: Homo sapiens

<400> SEQUENCE: 109

Gly Phe Thr Phe Asn Ser Phe Ala
1               5

<210> SEQ ID NO 110
<211> LENGTH: 8
<212> TYPE: PRT
<213> ORGANISM: Homo sapiens

<400> SEQUENCE: 110

Ala Lys Gly His Ala Phe Asp Ile
1               5

<210> SEQ ID NO 111
<211> LENGTH: 11
<212> TYPE: PRT
<213> ORGANISM: Homo sapiens

<400> SEQUENCE: 111

Gln Ser Leu Leu His Ser Asp Gly Lys Thr Tyr
1               5                   10

<210> SEQ ID NO 112
<211> LENGTH: 3
<212> TYPE: PRT
<213> ORGANISM: Homo sapiens

<400> SEQUENCE: 112

Glu Val Ser
1

<210> SEQ ID NO 113
<211> LENGTH: 9
<212> TYPE: PRT
<213> ORGANISM: Homo sapiens

<400> SEQUENCE: 113

Met Gln Ser Ile Gln Leu Pro Leu Thr
1               5

<210> SEQ ID NO 114
<211> LENGTH: 10
```

-continued

<212> TYPE: PRT
<213> ORGANISM: Homo sapiens

<400> SEQUENCE: 114

Ala Lys Asp Lys Gly Gly Gly Phe Asp Pro
1               5                   10

<210> SEQ ID NO 115
<211> LENGTH: 8
<212> TYPE: PRT
<213> ORGANISM: Homo sapiens

<400> SEQUENCE: 115

Ser Gly Ser Ile Ala Ser Asn Tyr
1               5

<210> SEQ ID NO 116
<211> LENGTH: 3
<212> TYPE: PRT
<213> ORGANISM: Homo sapiens

<400> SEQUENCE: 116

Glu Asp Asn
1

<210> SEQ ID NO 117
<211> LENGTH: 9
<212> TYPE: PRT
<213> ORGANISM: Homo sapiens

<400> SEQUENCE: 117

Gln Ser Tyr Asp Ser Thr Ser His Val
1               5

<210> SEQ ID NO 118
<211> LENGTH: 8
<212> TYPE: PRT
<213> ORGANISM: Homo sapiens

<400> SEQUENCE: 118

Ile Tyr Pro Gly Asp Ser Asp Thr
1               5

<210> SEQ ID NO 119
<211> LENGTH: 17
<212> TYPE: PRT
<213> ORGANISM: Homo sapiens

<400> SEQUENCE: 119

Ala Arg Pro Gly Tyr Tyr Tyr Gly Ser Gly Ser Tyr Tyr Asn Val Asp
1               5                   10                  15

Tyr

<210> SEQ ID NO 120
<211> LENGTH: 6
<212> TYPE: PRT
<213> ORGANISM: Homo sapiens

<400> SEQUENCE: 120

Glu Leu Gly Asp Lys Phe
1               5

<210> SEQ ID NO 121
<211> LENGTH: 3

```
<212> TYPE: PRT
<213> ORGANISM: Homo sapiens

<400> SEQUENCE: 121

Gln Asp Ser
1

<210> SEQ ID NO 122
<211> LENGTH: 10
<212> TYPE: PRT
<213> ORGANISM: Homo sapiens

<400> SEQUENCE: 122

Gln Val Trp Asp Ser Asn Gly Gly Pro Pro
1               5                   10
```

GLUCOCORTICOID-INDUCED TUMOR NECROSIS FACTOR RECEPTOR (GITR) ANTIBODIES AND METHODS OF USE THEREOF

RELATED APPLICATIONS

This application is a National Stage Entry of PCT/US2017/043504 filed on Jul. 24, 2017 which claims priority to, and the benefit of, U.S. Provisional Application No. 62/365,712 filed on Jul. 22, 2016 and U.S. Provisional Application No. 62/375,634 filed Aug. 16, 2016 the contents of which are incorporated herein by reference in their entireties.

FIELD OF THE INVENTION

This invention relates generally to anti-glucocorticoid-induced tumor necrosis factor receptor (GITR) antibodies as well as to methods for use thereof.

INCORPORATION-BY-REFERENCE OF SEQUENCE LISTING

The contents of the text file named 5031461-40-US3_SL.txt, which was created on Feb. 4, 2019 and is 51,691 bytes in size, are hereby incorporated by reference in their entirety.

BACKGROUND OF THE INVENTION

The immune system must achieve a balance between effective responses to eliminate pathogenic entities (e.g. in cancer), while maintaining tolerance to prevent autoimmune disease. T cells serve a critical role in maintaining a balance between suppression of immune function, and active immune rejection. T regulatory cells (Tregs) are characterized by the expression of CD25+, CD4+, FOXp3+ and glucocorticoid-induced tumor necrosis factor-related receptor (GITR). Tregs suppress pathological immune responses, and ultimately maintain immune homeostasis by way of regulating immunological self-tolerance. The presence of Tregs suppresses the activity of activated, effector T cells which are responsible for eliminating various pathological entities.

Human epithelial malignancies have been associated with the presence of increased amounts of Tregs both in the circulation and within the tumor itself. The increased presence of suppressive Tregs in cancer patients, results in a suppression of conventional T cells, including effector cells, which in turn leads to a downregulation in IFN-γ production. Reduction of the presence or the activity of Tregs in in vivo cancer animal models has resulted in an increase in the amounts and activity of effector T cells, which is often followed by a decrease in size of the tumor and or alleviation of other cancer symptoms.

T cell activation results in an upregulation of GITR levels in both Tregs and effector T cells. Manners of modulating the activity of GITR, such that the Tregs immune suppressing function is reduced, and the activity of effector T cells is increased is an ongoing area of intense study. The GITR ligand, GITR-L, is expressed in a variety of cells including dendritic cells, macrophages and B cells. Previous studies have shown an association between increased anti-tumor immune activity following administration of exogenous GITR-L, or by alternate means of antagonizing GITR, in cancer models.

Given the increased presence, and the role that Tregs have in cancer, further attention to modulating the activity and presence of Tregs, via GITR, is paramount in further understanding and, ultimately, in the treatment of cancer. Therefore, there exists an urgent need for agents that can specifically bind and modulate the binding of GITR with its ligand, GITR-L, as a means to promote effector T cell activity and, as a result, anti-tumor activity.

SUMMARY OF THE INVENTION

In various aspects the invention provides an an isolated humanized monoclonal antibody or antigen-binding fragment thereof that binds to the human anti-glucocorticoid-induced tumor necrosis factor receptor (GITR). The antibody has a variable heavy chain region having the amino acid sequence of SEQ ID NO: 2, and a variable light chain region having the amino acid sequence of SEQ ID NO: 4; a variable heavy chain region having the amino acid sequence of SEQ ID NO: 6, and a variable light chain region having the amino acid sequence of SEQ ID NO: 8; a variable heavy chain region comprising the amino acid sequence of SEQ ID NO: 10, and a variable light chain region having the amino acid sequence of SEQ ID NO: 12; a variable heavy chain region having the amino acid sequence of SEQ ID NO: 14, and a variable light chain region having the amino acid sequence of SEQ ID NO: 16; a variable heavy chain region having the amino acid sequence of SEQ ID NO: 18, and a variable light chain region having the amino acid sequence of SEQ ID NO: 20; a variable heavy chain region having the amino acid sequence of SEQ ID NO: 22, and a variable light chain region having the amino acid sequence of SEQ ID NO: 24; a variable heavy chain region having the amino acid sequence of SEQ ID NO: 26, and a variable light chain region having the amino acid sequence of SEQ ID NO: 28; a variable heavy chain region having the amino acid sequence of SEQ ID NO: 30, and a variable light chain region having the amino acid sequence of SEQ ID NO: 32; a variable heavy chain region having the amino acid sequence of SEQ ID NO: 34, and a variable light chain region having the amino acid sequence of SEQ ID NO: 36; a variable heavy chain region having the amino acid sequence of SEQ ID NO: 38, and a variable light chain region having the amino acid sequence of SEQ ID NO: 40; a variable heavy chain region having the amino acid sequence of SEQ ID NO: 42, and a variable light chain region having the amino acid sequence of SEQ ID NO: 44; a variable heavy chain region having the amino acid sequence of SEQ ID NO: 46, and a variable light chain region having the amino acid sequence of SEQ ID NO: 48; a variable heavy chain region having the amino acid sequence of SEQ ID NO: 50, and a variable light chain region having the amino acid sequence of SEQ ID NO: 52.

In a further aspect the invention provides an isolated humanized monoclonal antibody or antigen-binding fragment having a variable heavy chain complementarity determining region 1, 2, or 3 (VH-CDR) having the amino acid sequences of SEQ ID NO. 53, 54 or 55, respectively; and, a variable light chain complementarity determining region 1, 2 or 3 (VL-CDR) comprising the amino acid sequences of SEQ ID NO. 56, 57, or 58; a variable heavy chain complementarity determining region 1, 2, or 3 (VH-CDR) having the amino acid sequences of SEQ ID NO. 59, 60, or 61, respectively; and, a variable light chain complementarity determining region 1, 2 or 3 (VL-CDR) having the amino acid sequences of SEQ ID NO. 62, 63, or 64; a variable heavy chain complementarity determining region 1, 2, or 3

(VH-CDR) having the amino acid sequences of SEQ ID NO. 65, 66, or 67, respectively; and, a variable light chain complementarity determining region 1, 2 or 3 (VL-CDR) having the amino acid sequences of SEQ ID NO. 68, 69, or 70; a variable heavy chain complementarity determining region 1, 2, or 3 (VH-CDR) having the amino acid sequences of SEQ ID NO. 71, 72, or 73, respectively; and, a variable light chain complementarity determining region 1, 2 or 3 (VL-CDR) having the amino acid sequences of SEQ ID NO. 74, 75, or 76; a variable heavy chain complementarity determining region 1, 2, or 3 (VH-CDR) having the amino acid sequences of SEQ ID NO. 77, 78, or 79, respectively; and, a variable light chain complementarity determining region 1, 2 or 3 (VL-CDR) having the amino acid sequences of SEQ ID NO. 80, 81, or 82; a variable heavy chain complementarity determining region 1, 2, or 3 (VH-CDR) having the amino acid sequences of SEQ ID NO. 83, 84, or 85, respectively; and, a variable light chain complementarity determining region 1, 2 or 3 (VL-CDR) having the amino acid sequences of SEQ ID NO. 86, 87, or 88; a variable heavy chain complementarity determining region 1, 2, or 3 (VH-CDR) having the amino acid sequences of SEQ ID NO. 65, 72, or 89, respectively; and, a variable light chain complementarity determining region 1, 2 or 3 (VL-CDR) having the amino acid sequences of SEQ ID NO. 90, 91, or 92; a variable heavy chain complementarity determining region 1, 2, or 3 (VH-CDR) having the amino acid sequences of SEQ ID NO. 93, 94, or 95, respectively; and, a variable light chain complementarity determining region 1, 2 or 3 (VL-CDR) having the amino acid sequences of SEQ ID NO. 96, 97, or 98; a variable heavy chain complementarity determining region 1, 2, or 3 (VH-CDR) having the amino acid sequences of SEQ ID NO. 99, 100, or 101, respectively; and, a variable light chain complementarity determining region 1, 2 or 3 (VL-CDR) having the amino acid sequences of SEQ ID NO. 102, 103, or 104; a variable heavy chain complementarity determining region 1, 2, or 3 (VH-CDR) having the amino acid sequences of SEQ ID NO. 65, 72, or 105, respectively; and, a variable light chain complementarity determining region 1, 2 or 3 (VL-CDR) having the amino acid sequences of SEQ ID NO. 106, 107, or 108; a variable heavy chain complementarity determining region 1, 2, or 3 (VH-CDR) having the amino acid sequences of SEQ ID NO. 109, 72, or 110, respectively; and, a variable light chain complementarity determining region 1, 2 or 3 (VL-CDR) having the amino acid sequences of SEQ ID NO. 111, 112, or 113; a variable heavy chain complementarity determining region 1, 2, or 3 (VH-CDR) having the amino acid sequences of SEQ ID NO. 65, 72, or 114, respectively; and, a variable light chain complementarity determining region 1, 2 or 3 (VL-CDR) having the amino acid sequences of SEQ ID NO. 115, 116, or 117; and a variable heavy chain complementarity determining region 1, 2, or 3 (VH-CDR) having the amino acid sequences of SEQ ID NO. 101, 118, or 119, respectively; and, a variable light chain complementarity determining region 1, 2 or 3 (VL-CDR) having the amino acid sequences of SEQ ID NO. 120, 121, or 122.

The antibody is monovalent or bivalent. For example the antibody is a single chain antibody. The antibody has a binding affinity within the range of $10^{-5}$ M to $10^{-12}$ M. In some aspects the antibody has a IgG4 heavy chain constant region. In other aspects the antibody has an Fc region that contains mutations at amino acid positions 234 and 235. The mutations are for example, L234A and L235A.

In other aspects the invention includes a bi-specific antibody containing the human GITR antibody of the invention and an antibody that also binds to a tumor-associated antigen, a cytokine or a cell surface receptor.

Optionally the antibodies of the invention are s linked to a therapeutic agent, such as a toxin, a radiolabel, a siRNA, a small molecule, or a cytokine.

Also provide by the invention are cells producing the antibody according to the invention.

In various aspects the invention provides methods for depleting regulatory T-cells in a subject, by administering to a subject in need thereof a composition comprising an antibody according to the invention.

Other methods of the invention include augmenting an immune response to an antigen by administering to a subject in need thereof a composition comprising an antibody according to the invention. The antigen is a viral antigen, a bacterial antigen or a tumor associated antigen.

In various aspects administering an antibody according to the invention result in an increase in antigen specific T cell activity and/or an increase NK cell cytoxicity.

In some aspects the methods of the invention further includes administering to the subject IL-15.

In yet another aspect the invention includes methods of treating or alleviating a symptom of cancer by administering to a subject in need thereof a composition comprising an antibody according to the invention. The cancer is a cancer in which GITR or its ligand, GITR-L, is overexpressed. Optionally the subject is further administered a cytokine, such as IL-15 or a chemotherapeutic agent.

The invention further provides a nucleic acid having the nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, and 51.

In a further aspect the invention provides A nucleic acid encoding the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52 or polypeptide having the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52. Vectors containing the nucleic acids according to the invention are also provided. Also included in the invention are cells containing the vectors according to the invention.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1 illustrates the design and results from an ELISA in vitro binding assay used for identifying anti-GITR antibodies. Plates were coated with 2 ug/ml each of the A) hGITR-His; B) hGITR-mIgG2a; C) mGITR-His; or D) mIgG2a. OD measurements for each corresponding well are shown below the template.

FIG. 2 is a pair of graphs showing binding activity of indicated anti-GITR phage antibodies in four different concentrations (1E10 to 1E13 particles/mL) to two different concentrations of hGITR-mIg determined by a meso scale discovery immunoassay.

FIG. 4 illustrates the data for the flow cytometry binding assay performed using anti-GITR phage antibodies. Four concentrations of anti-GITR phage AB were tested along with CHO cells expressing either stable GITR or control CA9.

FIG. 5 is a graph showing flow cytometry GITR binding data with a single concentration of phage antibodies from culture supernatant of individual colonies. Orange bars indicate binding to CHO cells expressing GITR and blue bars indicate binding to CHO cells lacking GITR expression (CA9 control).

FIG. 6 illustrates ELISA GITR binding data for phage supernatant from single colonies. The clone template, OD450 for individual clones and the coating pattern for each plate is shown.

FIG. 7 illustrates flow cytometry and ELISA results for anti-GITR antibodies according to the invention.

DETAILED DESCRIPTION

Figure 3:
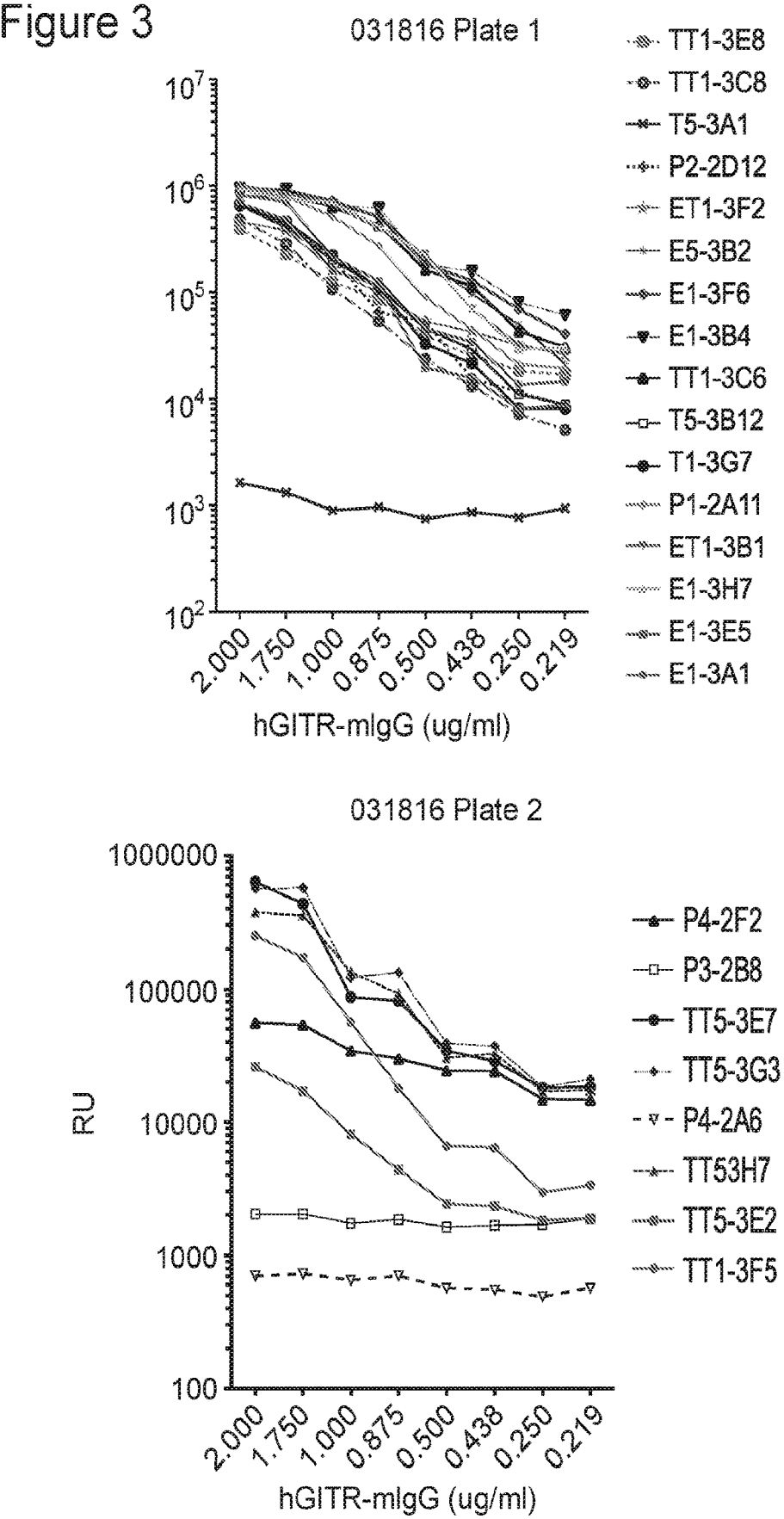
FIG. 3 is a pair of graphs showing binding activity for indicated anti-GITR phage antibodies to eight different concentrations of hGITR-mIg using a meso scale discovery immunoassay.

The present invention provides humanized monoclonal antibodies specific against glucocorticoid-induced tumor necrosis factor receptor, also known as GITR. The antibodies were identified through the use of extensively validated Mehta I/II human antibody-phage display libraries panning against human GITR. These antibodies represent a new class of human monoclonal antibodies against GITR.

These anti-GITR human monoclonal antibodies are referred to herein as "huGITR antibodies".

There is documented evidence of an increase in the amounts of regulatory T-cells (Tregs) in cases of epithelial cancers. There is also evidence that GITR plays a key role in the dominant immunological self-tolerance maintained by Tregs. This connection between GITR expression on the Tregs, and the increase in Tregs during cancer, allows for an opportunity to target GITR activity as a means to promote enhanced effector T cell function. Specifically, this makes targeting GITR, a potential immunotherapeutic approach to cancer treatment.

Tregs express CD28, CD4, FOXP3, and GITR. The suppression of effector T cell activity is largely mediated by way of FOXP3 dimerization with activated T cell nuclear factor, NF-AT, which in turn results in the suppression of IFN-γ, IL-2 and IL-4. Increased GITR ligation by means of binding with its ligand has been shown to reduce the suppressive effects that Tregs have on activated T cells. Additionally, antibodies that directly target GITR have also been shown to reduce Treg suppressive function.

While GITR is expressed in both Tregs and in effector T cells, the amount of expression of GITR is drastically greater in the former. As such, GITR has been considered a good candidate target for the modulation of the suppressive function of Tregs in various diseases, including cancer. Murine models have indicated that stimulation of the GITR results in reduced Treg suppressive activity. Other studies have also indicated that antagonizing GITR activity results in a lessening of Treg recruitment to malignant cells. Combined, these data indicate GITR as a crucial receptor in the pathophysiology of cancer.

The present invention provides a human monoclonal antibody that specifically binds GITR proteins. Binding of the antibody of the present invention to GITR interrupts the GITR ligand's ability to bind to GITR. By a variety of mechanisms, the huGITR antibody reduces the suppressive function that Tregs have on effector cells. Administration of the huGITR antibody may result in Treg depletion, increased effector T cell (Teff) proliferation, increased antigen-specific T cell activity, and increased production of effector cytokines. In some instances, the huGITR antibody promotes or augments the antigen-specific immune response.

Accordingly, the huGITR antibodies of the invention are useful in modulating T-cell activity. In particular the huGITR antibodies can suppress Treg activity and stimulate Teff activity. Additionally, the huGITR antibodies of the invention increase NK-cell cytotoxicity and increase IFNγ secretion.

The huGITR antibody is monovalent or bivalent and comprises a single or double chain. Functionally, the binding affinity of the huGITR antibody is within the range of $10^{-5}$ M to $10^{-12}$ M. For example, the binding affinity of the huGITR antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-8}$ M to $10^{-11}$ M, from $10^{-9}$M to $10^{-11}$ M, from $10^{-10}$ M to $10^{-11}$M, from $10^{-5}$M to $10^{-10}$ M, from $10^{-6}$ M to $10^{-10}$ M, from $10^{-7}$ M to $10^{-10}$ M, from $10^{-8}$ M to $10^{-10}$ M, from $10^{-9}$M to $10^{-10}$ M, from $10^{-5}$M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$M to $10^{-7}$ M, from $10^{-6}$ M to $10^{-7}$ M or from $10^{-5}$ M to $10^{-6}$ M.

Furthermore, the antibody of the present invention comprises a therapeutic agent including, but not limited to, a toxin, a radiolabel, a siRNA, or a cytokine.

Thirteen unique monoclonal huGITR antibodies were identified. These include mAb #E1-3B4, #E1-3E5 (and referred to as #P2-2D12), #E1-3E9, #E1-3H7 (also referred to as #E5-3B2 and #ET1-3B1), #ET1-3D6, #ET1-3E12, #P1-2A11, #P4-2F1, #T1-3G7, #TT1-3C6 (also referred to as #E1-3F6), TT1-3C8, #TT1-3F5, and #TT5-3E2. The variable region nucleic acid sequences and amino acid sequences are shown in Table 1A-13B. The amino acid sequences of the CDRs associated with the variable regions of these antibodies are shown in Table 14.

The nucleic acid and amino acid sequence of the monoclonal human GITR antibodies are provided below:

TABLE 1A

Ab #E1-3B4 Variable Region nucleic acid sequences

$V_H$ chain of Ab #E1-3B4 VH (IGHV3-9*01 F)         (SEQ ID NO: 1)
CAGGTGCAGCTGGTGCAGTCTGGGGGAGGCGTGGTACAGCCTGGGGGGTCCCTGAGACTCTCCTGTG
CAGCCTCTGGATTCACCTTTGATGATTATGCCATGCACTGGGTCCGGCAAGCTCCAGGGAAGGGCCT
GGAGTGGGTCTCAAGTCTTAGTTGGAATACTGGTCGAGTAGCCTATGCGGACTCTGTGAAGGGCCGA
TTCACCATCTCCAGAGACAACGCCAAGAATTCCCTGTATCTGCAAATGAACAGTCTGAGACCTGAGG
ACACGGCCTTCTATTACTGTGCAAAAGGCTCCGCCCTTGGCTTAGTTGGCTGGTTCGACGCCTGGGG
CCAGGGCACCCTGGTCACCGTCTCCTCAG $V_L$ chain of Ab #E1-3B4 (IGLV3-19*01)              (SEQ ID NO: 3)
TCTTCTGAGCTGACTCAGGACCCTGCTGTGTCTGTGGCCTTGGGACAGACAGTCAGGATCACATGCC
AAGGAGACAGTCTCAGAACCTATTATGGAAGTTGGTACCAGCAGAAGCCAGGACAGGCCCCTCTACT
TGTCTTCTATGGCAAAGAGAGTCGGCCCTCAGGGATCCCAGACCGATTCTCTGGCTCCACCTCAGGA
AACACAGCTTCCTTGACCATCACTGGGGCTCAGGCGGAAGATGAGGCTGACTATTACTGTAACTCCC
AGGACAGCAGTGGTGACTTATTATTCGGCGGAGGGACCAAGCTGACCGTCCTAG

TABLE 1B

Ab #E1-3B4 Variable Region amino acid sequences

$V_H$ chain of Ab #E1-3B4 VH (IGHV3-9*01)         (SEQ ID NO: 2)
QVQLVQSGGGVVQPGGSLRLSCAASGFTFDDYAMHWVRQAPGKGLEWVSSLSWNTGRVAYADSVKGR
FTISRDNAKNSLYLQMNSLRPEDTAFYYCAKGSALGLVGWFDAWGQGTLVTVSS $V_L$ chain of Ab #E1-3B4 (IGLV3-19*01)              (SEQ ID NO: 4)
SSELTQDPAVSVALGQTVRITCQGDSLRTYYGSWYQQKPGQAPLLVFYGKESRPSGIPDRFSGSTSG
NTASLTITGAQAEDEADYYCNSQDSSGDLLFGGGTKLTVL

TABLE 2A

Ab #E1-3E5 Variable Region nucleic acid sequences

$V_H$ chain of Ab #E1-3E5 VH (IGHV3-9*01)         (SEQ ID NO: 5)
caggtgcagctggtgcaatctgggggaggcttggtccagtctgggaagtccgtgagactctcttgtg
cagcctctggattcacatttggtgattatgccatgcactgggtccggcaagctccaggaaagggcct
ggagtgggtcgcaggcattactaggaatagtggtcgcatagcctatgcggactttgtgaagggccga
ttcatcatctccagagacaacgccaagaactcactgtatctgcaaatgaacagcctgagagccgagg
acacggctgtgtattactgtgcgagcgaaatgactggggcttatgatatttggggccaagggaccac
ggtcaccgtctcctcag $V_L$ chain of Ab #E1-3E5 VL (IGLV3-19*01)         (SEQ ID NO: 7)
TCTTCTGAGCTGACTCAGGACCCTGCTGTGTCTGTGGCCTTGGGACAGACAGTCAGGATCACATGCC
AAGGAGACGGCCTCAGATACTATTATGCAAGCTGGTACCAGCAGAAGCCAGGACAGGCCCCTCTACT
TGTCCTCTTTGGTAAAAACAACCGGCCCTCAGGGATCCCAGACCGATTCTCTGGCTCCAGCTCAGGA
AATACAGCTTCCTTGACCATCACTGGGGCTCAGGCGGAAGATGAGGCTGACTATTACTGTAACTCGC
GGGACAGCAGTGGTAACCATCGATTCTTCGGAACTGGGACCAAGGTCACCGTCCTAA

TABLE 2B

Ab #E1-3E5 Variable Region amino acid sequences

$V_H$ chain of Ab #E1-3E5 (also #P2-2D12) VH (IGHV3-9*01)   (SEQ ID NO: 6)
QVQLVQSGGGLVQSGKSVRLSCAASGFTFGDYAMHWVRQAPGKGLEWVAGITRNSGRIAYADFVKGR
FIISRDNAKNSLYLQMNSLRAEDTAVYYCASEMTGAYDIWGQGTVTVSS $V_L$ chain of Ab #E1-3E5 (also #P2-2D12) VL (IGLV3-19*01)  (SEQ ID NO: 8)
SSELTQDPAVSVALGQTVRITCQGDGLRYYYASWYQQKPGQAPILVLFGKNNRPSGIPDRFSGSSSG
NTASLTITGAQAEDEADYYCNSRDSSGNHRFFGTGTKVTVL

TABLE 3A

Ab #E1-3E9 Variable Region nucleic acid sequences $V_H$ chain of Ab #E1-3E9 VH (IGHV3-30-3*01)  (SEQ ID NO: 9)
CAGGTGCAGCTGGTGCAGTCTGGGGGAGGCGTGGTCCAGCCTGGGAGGTCCCTGAGACTCTCCTGTG
CAGCCTCTGGATTCACCTTCAGTAGCTATGCTATGCACTGGGTCCGCCAGGCTCCAGGCAAGGGGCT
GGAGTGGGTGGCAGTTATATCATATGATGGAAGCAATAAATACTACGCAGACTCCGTGAAGGGCCGA
TTCACCATCTCCAGAGACAATTCCAAGAACACGCTGTATCTGCAAATGAACAGCCTGAGAGCTGAGG
ACACGGCTGTATATTACTGTGCGAAAGAGGATTACTATGATAGTAGTGGTTCGAACTACTGGGGCCA
GGGAACCCTGGTCACCGTCTCCTCAG $V_L$ chain of Ab #E1-3E9 VL (IGLV1-47*01)  (SEQ ID NO: 11)
CTGCCTGTGCTGACTCAGCCACCCTCAGCGTCTGGGACCCCCGGGCAGAGGGTCACCATCTCTTGTT
CTGGAAGCAGCTCCAACATCGGAAGTAATTATGTATACTGGTACCAGCAGCTCCCAGGAACGGCCCC
CAAACTCCTCACCTATAGGAATGATCAGCGGCCCTCAGGGGTCCCTGACCGATTCTCTGGCTCCAAG
TCTGCCACCTCAGCCTCCCTGGCCATCAGTGGGCTCCGGTCCGAGGATGAGGCTGATTATTTCTGTT
CAGCTTGGGATGACAGCCTGGGTGGCGAGGTCTTCGGAACTGGGACCAAGGTCAACGTCCTAG

TABLE 3B

Ab #E1-3E9 Variable Region amino acid sequences $V_H$ chain of Ab #E1-3E9 VH (IGHV3-30-3*01)  (SEQ ID NO: 10)
QVQLVQSGGGVVQPGRSLRLSCAASGFTFSSYAMHWVRQAPGKGLEWVAVISYDGSNKYYADSVKGR
FTISRDNSKNTLYLQMNSLRAEDTAVYYCAKEDYYDSSGSNYWGQGTLVTVSS $V_L$ chain of Ab #E1-3E9 VL (IGLV1-47*01)  (SEQ ID NO: 12)
LPVLTQPPSASGTPGQRVTISCSGSSSNIGSNYVYWYQQLPGTAPKLLTYRNDQRPSGVPDRFSGSK
SGTSASLAISGLRSEDEADYFCSAWDDSLGGEVEGTGTKVNVL

TABLE 4A

Ab #E1-3H7 Variable Region nucleic acid sequences $V_H$ chain of Ab #E1-3H7 VH (IGHV3-23*04)  (SEQ ID NO: 13)
CAGGTGCAGCTGGTGCAGTCTGGGGGAGGCTTGGTACAGCCTGGGGGGTCCCTGAGACTCTCCTGTG
CAGCCTCTGGATTCACCTTTAGCAGCCATGCCATGAGCTGGGTCCGCCAGGCTCCAGGGAAGGGGCT
GGAGTGGGTCTCAGCTATTAGTGGTAGTGGTGGTAGCACATACTACGCAGACTCCGTGAAGGGCCGG
TTCACCATCTCCAGAGACAATTCCAAGAACACGCTGTATCTGCAAATGAACAGCCTGAGAGCCGAGG
ACACGGCCGTATATTACTGTGCGAAAATCGGTACGGCGGATGCTTTTGATATCTGGGGCCAAGGGAC
CACGGTCACCGTCTCCTCAG $V_L$ chain of Ab #E1-3H7 VL (IGLV1-44*01)  (SEQ ID NO: 15)
CAGTCTGCCCTGACTCAGCCACCCTCAGTGTCTGGGACCCCCGGACAGAGGGTCACCATCTCTTGTT
CTGGAGGCGTCCCCAACATCGGAAGTAATCCTGTAAACTGGTACCTCCACCGCCCAGGAACGGCCCC
CAAACTCCTCATCTATAATAGCAATCAGTGGCCCTCAGGGGTCCCTGACCGATTTTCTGGCTCCAGG
TCTGCCACCTCAGCCTCCCTGGCCATCAGTGGGCTCCAGTCTGAGGATGAGGCTGATTATTACTGTG
CAGCATGGGATGACAGCCTGGATGGTCTGGTTTTCGGCGGAGGGACCAAGTTGACCGTCCTAG

TABLE 4B

Ab #E1-3H7 Variable Region amino acid sequences $V_H$ chain of Ab #E1-3H7 (also #E5-3B2 and #ET1-3B1)
VH (IGHV3-23*04)  (SEQ ID NO: 14)
QVQLVQSGGGLVQPGGSLRLSCAASGFTFSSHAMSWVRQAPGKGLEWVSAISGSGGSTY
YADSVKGRFTISRDNSKNTLYLQMNSLRAEDTAVYYCAKIGTADAFDIWGQGTTVTVSS $V_L$ chain of Ab #E1-3H7 (also #E5-3B2 and #ET1-3B1)
VL (IGLV1-44*01)  (SEQ ID NO: 16)
QSALTQPPSVSGTPGQRVTISCSGGVPNIGSNPVNWYLHRPGTAPKLLIYNSNQWPSGV
PDRFSGSRSGTSASLAISGLQSEDEADYYCAAWDDSLDGLVFGGGTKLTVL TABLE 5A #ET1-3D6 Variable Region nucleic acid sequences $V_H$ chain of #ET1-3D6 VH (IGHV1-46*01)     (SEQ ID NO: 17)
CAGGTGCAGCTGGTGCAGTCTGGGGCTGAGGTGAAGAAGCCTGGGGCCTCAGTGAAGGTTTCCTGCA
AGGCATCTGGATACACCTTCACCAGCTACTATATGCACTGGGTGCGACAGGCCCCTGGACAAGGGCT
TGAGTGGATGGGAATAATCAACCCTAGTGGTGGTAGCACAAGCTACGCACAGAAGTTCCAGGGCAGA
GTCACCATGACCAGGGACACGTCCACGAGCACAGTCTACATGGAGCTGAGCAGCCTGAGATCTGAGG
ACACGGCCGTGTATTACTGTGCTAGAGAAAAAAGCAGCAGCTGGTACGGGGGGGACAACTGGTTCGA
CCCCTGGGGCCAGGGCACCCTGGTCACCGTCTCCTCAG $V_L$ chain of #ET1-3D6 VL (IGLV2-11*01)     (SEQ ID NO: 19)
CAGTCTGCCCTGACTCAGCCTCGCTCAGTGTCCGGGTCTCCTGGACAGTCAGTCACCATCTCCTGCA
CTGGAAGCAGCAGTGATGTTGGTGGTTATCATTATGTCTCCTGGTACCAACAATACCCAGGCWGT
CCCCAAACTGATGATTTATGATGTCTCTAGGCGGCCCTCAGGGGTTTCTGATCGCTTCTCTGGCTCC
AAGTCTGGCAGCACGGCCTCCCTGACCATCTCTGGGCTCCAGGCTGAGGACGAGGCTGATTATTACT
GCAGCTCATATACAAGCAGCAGCACTGTGGTCTTCGGCGGAGGGACCAAGCTGACCGTCCTAC

TABLE 5B

ET1-3D6 Variable Region amino acid sequences $V_H$ chain of #ET1-3D6 VH (IGHV1-46*01)     (SEQ ID NO: 18)
QVQLVQSGAEVKKPGASVKVSCKASGYTFTSYYMHWVRQAPGQGLEWMGIINPSGGSTSYAQ
KFQGRVTMTRDTSTSTVYMELSSLRSEDTAVYYCAREKSSSWYGGDNWFDPWGQGTLVTVSS $V_L$ chain of #ET1-3D6 VL (IGLV2-11*01)     (SEQ ID NO: 20)
QSALTQPRSVSGSPGQSVTISCTGSSSDVGGYHYVSWYQQYPGKVPKLMIYDVSRRPSGVSD
RFSGSKSGSTASLTISGLQAEDEADYYCSSYTSSSTVVFGGGTKLTVL

TABLE 6A

ET1-3E12 Variable Region nucleic acid sequences $V_H$ chain of #ET1-3E12 VH (IGHV1-18*01)     (SEQ ID NO: 21)
CAGGTGCAGCTGGTGCAATCTGGAGCTGAGGTGAAGAAGCCTGGGGCCTCAGTGAAGGTCTCCTGCA
AGGCTTCTGGTTACACCTTTACCAGCTATGGTATCAGCTGGGTGCGACAGGCCCCTGGACAAGGGCT
TGAGTGGATGGGATGGATCAGCGCTTACAATGGTAACACAAACTATGCACAGAAGCTCCAGGGCAGA
GTCACCATGACCACAGACACATCCACGAGCACAGCCTACATGGAGCTGAGGAGCCTGAGATCTGACG
ACACGGCCGTGTATTACTGTGCGAGAGATGTACACCCCTTAGATATAGCAGTGGCTGCCGACGATTA
CTACTACTACGGTATGGACGTCTGGGGCCAAGGCACCCTGGTCACCGTCTCCTCA $V_L$ chain of #ET1-3E12 VL (IGLV3-19*01)     (SEQ ID NO: 23)
TCTTCTGAGCTGACTCAGGACCCTGCTGTGTCTGTGGCCTTGGGACAGACAGTCAGGATCACATGCC
AAGGAGACAGCCTCACAACCAATTATGCAAGCTGGTACCAGCAGAAGCCAGGACAGGCCCCTGTTCT
TGTCATCTATGGTAAAAACAAGCGGCCCTCAGGGATCCCAGACCGATTCTCTGGCTCCATCTCAGGG
AACACAGCTTCCTTGACCATCACTGGGGCTCAGGCGGAGGATGAGGCTGACTATTACTGTAACTCCC
GGGACAGCAGTGGTAAGCATTATGTCTTCGGAACTGGGACCAAGGTCACCGTCCTAG

TABLE 6B

ET1-3E12 Variable Region amino acid sequences $V_H$ chain of #ET1-3E12 VH (IGHV1-18*01)     (SEQ ID NO: 22)
QVQLVQSGAEVKKPGASVKVSCKASGYTFTSYGISWVRQAPGQGLEWMGWISAYNGNTNYAQKLQGR
VTMTTDTSTSTAYMELRSLRSDDTAVYYCARDVHPLDIAVAADDYYYYGMDVWGQGTLVTVSS $V_L$ chain of #ET1-3E12 VL (IGLV3-19*01)     (SEQ ID NO: 24)
SSELTQDPAVSVALGQTVRITCQGDSLTTNYASWYQQKPGQAPVLVIYGKNKRPSGIPDRFSGSISG
NTASLTITGAQAEDEADYYCNSRDSSGKHYVFGTGTKVTVL

TABLE 7A

P1-2A11 Variable Region nucleic acid sequences $V_H$ chain of #P1-2A11 VH (IGHV3-23*04)  (SEQ ID NO: 25)
GAGGTGCAGCTGGTGGAGTCTGGGGGAGGCGTGGTCCAGCCTGGGAGGTCCCTGAGACTCTCCTGTG
CAGCCTCTGGATTCACCTTTAGCAGCTATGCCATGAGCTGGGTCCGCCAGGCTCCAGGGAAGGGGCT
GGAGTGGGTCTCAGCTATTAGTGGTAGTGGTGGTAGCACATACTACGCAGACTCCGTGAAGGGCCGG
TTCACCATCTCCAGAGACAATTCCAAGAACACGCTGTATCTGCAAATGAACAGCCTGAGAGCCGAGG
ACACGGCCGTATATTACTGTGCGAAAGATTGGGGCCTAGTACAACTGGAATCCGGCTATGACTACTG
GGGCCAGGGAACCCTGGTCACCGTCTCCTCAG $V_L$ chain of #P1-2A11 VL (IGLV1-50*01)  (SEQ ID NO: 27)
CAGTCTGTGCTGACTCAGCCACCCTCAGTGTCTGGGGCCCCAGGGCAGAGGGTCACCATCTCCTGCA
CTGGGAGCAGCTCCAACATCGGGGCAGGTTATGATGTACACTGGTACCAACAGCTTCCAGGAAAAGC
CCCCAAACTCCTCATCTATGATAATACCAATCGGCCCTCGGGGGTCCCTGACCGATTCTCTGGCTCC
AAGTCTGGCACCTCAGCCTCCCTGGCCATCAGTGGGCTCCAGTCTGAGGATGAGGCTGATTATTACT
GTGCAGCATGGGATGAAAGCCTGAATGGTCAGGTCTTCGGAACTGGGACCAAGGTCACCGTCCTAG

TABLE 7B

P1-2A11 Variable Region amino acid sequences $V_H$ chain of #P1-2A11 VH (IGHV3-23*04 F)  (SEQ ID NO: 26)
EVQLVESGGGVVQPGRSLRLSCAASGFTFSSYAMSWVRQAPGKGLEWVSAISGSGGSTYYADSVKGR
FTISRDNSKNTLYLQMNSLRAEDTAVYYCAKDWGLVQLESGYDYWGQGTLVTVSS $V_L$ chain of #P1-2A11 VL (IGLV1-50*01)  (SEQ ID NO: 28)
QSVLTQPPSVSGAPGQRVTISCTGSSSNIGAGYDVHWYQQLPGKAPKLLIYDNTNRPSGVPDRFSGS
KSGTSASLAISGLQSEDEADYYCAAWDESLNGQVFGTGTKVTVL

TABLE 8A

P4-2F1 Variable Region nucleic acid sequences $V_H$ chain of #P4-2F1 VH (IGHV4-4*02)  (SEQ ID NO: 29)
CAGGTACAGCTGCAGCAGTCAGGCCCAGGACTGGTGAAGCCTTCGGGGACCCTGTCCCTCACCTGCG
CTGTCTCTGGTGGCTCCATCAGCAGTAGTGACTGGTGGAGTTGGGTCCGCCAGGTCCCAGGGAAGGG
GCTGGAGTGGATTGGGGAAATCTATCACAGTGGCAGTCCCAACTACAACCCGTCCCTCAGGGGTCGA
GTCACCATATCAGTAGACAAGTCGAAGAACCAGTTCTCCCTGAAGCTGAGCTCTGTGACCGCCGCGG
ACACGGCCGTCTATTACTGTGCGAGAGAAAGAGTTGCTCCTACAGTAGACGGTGCTTTTGATGTCTG
GGGCCAAGGGACAATGGTCACCGTCTCCTCAG $V_L$ chain of #P4-2F1 VL (IGKV1-39*01)  (SEQ ID NO: 31)
GACATCGTGATGACCCAGTCTCCATCCTCCCTGTCTGCATCTGTAGGAGACAGAGTCACCATCACTT
GCCGGGCAAGTCAGAGCATTACCACCTATTTAAATTGGTATCAGCAGAAACCAGGGAAAGCCCCTAA
GCTCCTGATCTATGCTGCATCCAGTTTGCAAAGTGGGGTCCCATCAAGGTTCAGTGGCAGTGGATCT
GGGACAGAATTCACTCTCACTATCAGCAGCCTGCAGCCTGAAGATTTTGCAACTTATTATTGTCAAC
AGGCCAGCAGTTTCCCTCTCACTTTCGGCGGAGGGACCAAGGTGGATCTCAAAC

TABLE 8B

P4-2F1 Variable Region amino acid sequences $V_H$ chain of #P4-2F1 VH (IGHV4-4*02)  (SEQ ID NO: 30)
QVQLQQSGPGLVKPSGTLSLTCAVSGGSISSSDWWSWVRQVPGKGLEWIGEIYHSGSPNYNPSLRGR
VTISVDKSKNQFSLKLSSVTAADTAVYYCARERVAPTVDGAFDVWGQGTMVTVSS $V_L$ chain of #P4-2F1 VL (IGKV1-39*01 F)  (SEQ ID NO: 32)
DIVMTQSPSSLSASVGDRVTITCRASQSITTYLNWYQQKPGKAPKLLIYAASSLQSGVPSRFSGSGS
GTEFTLTISSLQPEDFATYYCQQASSFPLTFGGGTKVDLK

TABLE 9A

T1-3G7 Variable Region nucleic acid sequences

V_H chain of #T1-3G7 VH (IGHV5-51*01)    (SEQ ID NO: 33)
GAGGTGCAGCTGGTGCAGTCTGGAGCTGAGGTGAAAAAGCCCGGGGAGTCTCTGAAGATCTCCTGTA
AGGGTTCGGGATACAGCTTTACCAACTACTGGATCGGCTGGGTGCGCCAGATGCCCGGGAAAGGCCT
GGAGTGGATTGGGATCATCTATCCTGGTGACTCTGATACCAGATACAGCCCGTCCTTCCAAGGCCAG
GTCACCATCTCAGCCGACAAGTCCACCAGCACTGCCTACCTGCAGTGGAGCAGCCTGAAGGCCTCGG
ACACCGCCATGTATTACTGTGCGAGGATAAAGAGTTACTATGATAGTAGTGGTTATTACCTCTGGGG
CCAGGGAACCCTGGTCACCGTCTCCTCAG V_L chain of #T1-3G7 VL (IGLV3-21*02)    (SEQ ID NO: 35)
CAGTCTGTGCTGACTCAGCCACCCTCGGTGTCAGTGGCCCCAGGACAGACGGCCAGCATAACCTGTG
GGGGAAACAACATTGGGAGTAAAAGTGTGCACTGGTACCAGCAGAAGCCAGGCCAGGCCCCTGTCCT
GGTCGTCTATGATGATAGCGACCGGCCCTCAGGGATCCCTGAGCGATTCTCTGGCTCCAACTCTGGG
AACACGGCCACCCTGACCATCAGCAGGGTCGAAGCCGGGGATGAGGCCGACTATTACTGTCAGGTGT
GGGATAGTAGTAGTGAAGAGGTATTCGGCGGAGGGACCAAGCTGACCGTCCTAG

TABLE 9B

T1-3G7 Variable Region amino acid sequences

V_H chain of #T1-3G7 VH (IGHV5-51*01)    (SEQ ID NO: 34)
EVQLVQSGAEVKKPGESLKISCKGSGYSETNYWIGWVRQMPGKGLEWIGIIYPGDSDTRYSPSFQGQ
VTISADKSTSTAYLQWSSLKASDTAMYYCARIKSYYDSSGYYLWGQGTLVTVSS V_L chain of #T1-3G7 VL (IGLV3-21*02)    (SEQ ID NO: 36)
QSVLTQPPSVSVAPGQTASITCGGNNIGSKSVHWYQQKPGQAPVLVVYDDSDRPSGIPERFSGSNSG
NTATLTISRVEAGDEADYYCQVWDSSSEEVFGGGTKLTVL

TABLE 10A

TT1-3C6 (also #E1-3F6) Variable Region nucleic acid sequences

V_H chain of #TT1-3C6 VH (IGHV3-23*04)    (SEQ ID NO: 37)
GAGGTGCAGCTGGTGCAGTCTGGGGGAGGCTTGGTACAGCCTGGGGGGTCCCTGAGACTCTCCTGTG

CAGCCTCTGGATTCACCTTTAGCAGCTATGCCATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGACG

ACACGGCTGTCTATTACTGTGCGAGAAGGGGGTTCATGGACGTCTGGGGCAAAGGCACCCTGGTCAC

CGTCTCCTCAG

V_L chain of #TT1-3C6 VL (IGLV3-19*01)    (SEQ ID NO: 39)
TCTTCTGAGCTGACTCAGGACCCTGCTGTGTCTGTGGCCTTGGGACAGACAGTCACCATCACATGCC

AAGGAGACATCCTCGAAGCCTATTATGCAAGTTGGTACCAGCAGAGGCCAGGACAGGCCCCTGTCCT

TGTCATCTATGGCGAAAACAACCGGCCCTCAGGGATCCCAGACCGGTTCTCTGGCTCCAGGTCAGGA

AACACAGCCTCCTTGACCATCACTGGGGCTCAGGCGGAAGATGAGGCTGACTATTATTGTAACTCTC

GGGACAGCAGTGGTAGCCATGTGGTATTCGGCGGAGGGACCAAGATGACCGTCCTGG

TABLE 10B

TT1-3C6 (also #3F6) Variable Region amino acid sequences

V_H chain of #TT1-3C6 VH (IGHV3-23*04)    (SEQ ID NO: 38)
EVQLVQSGGGLVQPGGSLRLSCAASGFTFSSYAMSWVRQAPGKGLEWVSAISGSGGSTYYADSVKGR
FTISRDNSKNTLYLQMNSLRADDTAVYYCARRGFMDVWGKGTLVTVSS V_L chain of #TT1-3C6 VL (IGLV3-19*01)    (SEQ ID NO: 40)
SSELTQDPAVSVALGQTVTITCQGDILEAYYASWYQQRPGQAPVLVIYGENNRPSGIPDRFSGSRSG
NTASLTITGAQAEDEADYYCNSRDSSGSHVVFGGGTKMTVL

TABLE 11A

#TT1-3C8 Variable Region nucleic acid sequences

V_H chain of #TT1-3C8 VH (IGHV3-23*04)  (SEQ ID NO: 41)
CAGGTGCAGCTGGTGCAGTCTGGGGGAGGCTTGGTACAGCCTGGGGGGTCCCTGAGACTCTCCTGTG
CAGCCTCTGGATTCACCTTTAACAGCTTTGCCATGACCTGGGTCCGCCAGGCTCCAGGGAAGGGGCT
GGAGTGGGTCTCAGGTATTAGTGGTAGTGGTGGTAGCACATACTACGCAGACTCCGTGAAGGGCCGG
TTCACCATCTCCAGAGACAATTCCAAGAACACGCTGTATCTGCAAATGAACAGCCTGAGAGCCGAGG
ACACGGCCGTATATTACTGTGCGAAAGGGCACGCTTTTGATATCTGGGGCCAAGGGACCACGGTCAC
CGTCTCCTCAG V_L chain of #TT1-3C8 VL (IGKV2D-29*01)  (SEQ ID NO: 43)
GACATCGTGATGACCCAGTCTCCACTCTCTCTGTCCGTCACCCCTGGGCAGCCGGCCTCCATCTCCT
GCAAGTCTAGTCAGAGCCTCCTGCATAGTGATGGAAAGACCTATTTGTATTGGTACCTGCAGAAGCC
AGGCCAGCCTCCACAACTCCTGATCTATGAAGTTTCCAACCGGTTCTCTGGAGTGCCAGATAGGTTC
AGTGGCAGCGGGTCAGGGACAGATTTCACACTGAAAATCAGCCGGGTGGAGGCTGAGGATGTTGGGG
TTTATTACTGCATGCAAAGTATACAGCTTCCTCTCACTTTCGGCGGAGGGACCAAGGTGGAGATCAA
AC

TABLE 11B

#TT1-3C8 Variable Region amino acid sequences

V_H chain of #TT1-3C8 VH (IGHV3-23*04)  (SEQ ID NO: 42)
QVQLVQSGGGLVQPGGSLRLSCAASGFTFNSFAMTWVRQAPGKGLEWVSGISGSGGSTYYADSVKGR
FTISRDNSKNTLYLQMNSLRAEDTAVYYCAKGHAFDIWGQGTTVTVSS V_L chain of #TT1-3C8 VL (IGKV2D-29*01)  (SEQ ID NO: 44)
DIVMTQSPLSLSVTPGQPASISCKSSQSLLHSDGKTYLYWYLQKPGQPPQLLIYEVSNRFSGVPDRF
SGSGSGTDFTLKISRVEAEDVGVYYCMQSIQLPLTFGGGTKVEIK

TABLE 12A

#TT1-3F5 Variable Region nucleic acid sequences

V_H chain of #TT1-3F5 VH (IGHV3-23*04)  (SEQ ID NO: 45)
CAGGTGCAGCTGGTGCAGTCTGGGGGAGGCTTGGTACAGCCTGGGGGGTCCCTGAGACTCTCCTGTG

CAGCCTCTGGATTCACCTTTAGCAGCTATGCCATGAGCTGGGTCCGCCAGGCTCCAGGGAAGGGGCT

GGAGTGGGTCTCAGCTATTAGTGGTAGTGGTGGTAGCACATACTACGCAGACTCCGTGAAGGGCCGG

TTCACCATCTCCAGAGACAATTCCAAGAACACGCTGTATCTGCAAATGAACAGCCTGAGAGCCGAGG

ACACGGCTGTGTATTACTGTGCGAAAGATAAAGGTGGGGGGTTCGACCCCTGGGGCCAGGGAACCCT

GGTCACCGTCTCCTCAG

V_L chain of #TT1-3F5 VL (IGLV6-57*01)  (SEQ ID NO: 47)
AATTTTATGCTGACTCAGCCCCACTCTGTGTCGGAGTCTCCGGGGAAGACGGTAACCATCTCCTGCA

CCCGCAGCAGTGGCAGCATTGCCAGCAACTATGTGCAGTGGTACCAGCAGCGCCCGGGCAGTTCCCC

CACCACTGTGATCTATGAGGATAACCAAAGACCCTCTGGGGTCCCTGATCGGTTCTCTGGCTCCATC

GACAGCTCCTCCAACTCTGCCTCCCTCACCATCTCTGGACTGAAGACTGAGGACGAGGCTGACTACT

ACTGTCAGTCTTATGATAGTACCTCTCATGTCTTCGGAACTGGGACCCAGGTCACCGTCCTAG

TABLE 12B

#TT1-3F5 Variable Region amino acid sequences

V_H chain of #TT1-3F5 VH (IGHV3-23*04)  (SEQ ID NO: 46)
QVQLVQSGGGLVQPGGSLRLSCAASGFTFSSYAMSWVRQAPGKGLEWVSAISGSGGSTYYADSVKGR
FTISRDNSKNTLYLQMNSLRAEDTAVYYCAKDKGGGFDPWGQGTLVTVSS V_L chain of #TT1-3F5 VL (IGLV6-57*01)  (SEQ ID NO: 48)
NFMLTQPHSVSESPGKTVTISCTRSSGSIASNYVQWYQQRPGSSPTTVIYEDNQRPSGVPDRFSGSI
DSSSNSASLTISGLKTEDEADYYCQSYDSTSHVFGTGTQVTVL

TABLE 13A

TT5-3E2 Variable Region nucleic acid sequences $V_H$ chain of #TT5-3E2 VH (IGHV5-51*01)                (SEQ ID NO: 49)
GAGGTGCAGCTGGTGCAGTCTGGAGCAGAGGTGAAGCCCGGGGAGTCTCTGAAGATCTCCTGTA
AGGGTTCTGGATACAGCTTTACCAACTACTGGATCGGCTGGGTGCGCCAGATGCCCGGGAAAGGCCT
GGAGTGGGTGGGGATCATCTATCCTGGTGACTCTGATACCAGATACAGCCCGTCCTTCCAAGGCCAG
GTCACCATCTCAGCCGACAAGTCCATCAGCACCGCCTACCTGCAGTGGAGCAGCCTGAAGGCCTCGG
ACACCGCCATGTATTACTGTGCGAGACCAGGGTATTACTATGGTTCGGGGAGTTATTATAACGTTGA
CTACTGGGGCCAGGGCACCCTGGTCACCGTCTCCTCAG $V_L$ chain of #TT5-3E2 VL (IGLV3-1*01)                 (SEQ ID NO: 51)
CAGCCTGGGCTGACTCAGCCACCCTCAGTGTCCGTGTCCCCAGGACAGACAGCCAGCATCACCTGCT
CTGGAGATGAATTGGGGGATAAATTTGCTTTCTGGTATCAACAAAAGCCAGGCCAGTCCCCTGTGCT
GGTCATCTATCAAGATAGTAAGAGGCCCTCAGGGATCCCTGAGCGATTCTCTGGCTCCATCTCTGGG
AACACGGCCACCCTGACTATCAGCAGGGTCGAGGCCGGAGATGAGGCCGACTATTTCTGTCAGGTGT
GGGATAGCAATGGTGGTCCCCCATTCGGGAGAGGGACCAAGCTGACCGTCCTAG

TABLE 13B

TT5-3E2 Variable Region amino acid sequences $V_H$ chain of #TT5-3E2 VH (IGHV5-51*01)                (SEQ ID NO: 50)
EVQLVQSGAEVKKPGESLKISCKGSGYSFTNYWIGWVRQMPGKGLEWVGIIYPGDSDTRYSPSFQGQ
VTISADKSISTAYLQWSSLKASDTAMYYCARPGYYYGSGSYYNVDYWGQGTLVTVSS $V_L$ chain of #TT5-3E2 VL (IGLV3-1*01)                 (SEQ ID NO: 52)
QPGLTQPPSVSVSPGQTASITCSGDELGDKFAFWYQQKPGQSPVLVIYQDSKRPSGIPERFSGSISG
NTATLISRVEAGDEADYFCQVWDSNGGPPFGRGTKLTVL The huGITR antibodies described herein bind to GITR. In one aspect, the huGITR antibodies have high affinity and high specificity for GITR. In another aspect, the huGITR antibodies can bind the GITR receptor and prevent, inhibit, or block the ligand GITR-L from binding its receptor GITR.

TABLE 14

Amino Acid Sequences of Heavy and Light Chains.

| Antibody | Variable region | CDR1 | CDR2 | CDR3 |
| --- | --- | --- | --- | --- |
| #E1-3B4 | VH | GFTFDDYA (SEQ ID NO: 53) | LSWNTGRV (SEQ ID NO: 54) | AKGSALGLVGWFDA (SEQ ID NO: 55) |
| #E1-3B4 | VL | SLRTYY (SEQ ID NO: 56) | GKE (SEQ ID NO: 57) | NSQDSSGDLL (SEQ ID NO: 58) |
| #E1-3E5 (and #P2-2D12) | VH | GFTFGDYA (SEQ ID NO: 59) | ITRNSGRI (SEQ ID NO: 60) | ASEMTGAYDI (SEQ ID NO: 61) |
| #E1-3E5 (and P2-2D12) | VL | GLRYYY (SEQ ID NO: 62) | GKN (SEQ ID NO: 63) | NSRDSSGNHRF (SEQ ID NO: 64) |
| #E1-3E9 | VH | GFTFSSYA (SEQ ID NO: 65) | ISYDGSNK (SEQ ID NO: 66) | AKEDYYDSSGSNY (SEQ ID NO: 67) |
| #E1-3E9 | VL | SSNIGSNY (SEQ ID NO: 68) | RND (SEQ ID NO: 69) | SAWDDSLGGEV (SEQ ID NO: 70) |
| #E1-3H7 (also #E5-3B2 and #ET1-3B1) | VH | GFTFSSHA (SEQ ID NO: 71) | ISGSGGST (SEQ ID NO: 72) | AKIGTADAFDI (SEQ ID NO: 73) |

TABLE 14-continued

Amino Acid Sequences of Heavy and Light Chains.

| Antibody | Variable region | CDR1 | CDR2 | CDR3 |
|---|---|---|---|---|
| #E1-3H7 (also #E5-3B2 and #ET1-3B1) | VL | VPNIGSNP (SEQ ID NO: 74) | NSN (SEQ ID NO: 75) | AAWDDSLDGLV (SEQ ID NO: 76) |
| #ET1-3D6 | VH | GYTFTSYY (SEQ ID NO: 77) | INPSGGST (SEQ ID NO: 78) | AREKSSSWYGGDNWFDP (SEQ ID NO: 79) |
| #ET1-3D6 | VL | SSDVGGYHY (SEQ ID NO: 80) | DVS (SEQ ID NO: 81) | SSYTSSSTVV (SEQ ID NO: 82) |
| #ET1-3E12 | VH | GYTFTSYG (SEQ ID NO: 83) | ISAYNGNT (SEQ ID NO: 84) | ARDVHPLDIAVAADDYYYYGMDV (SEQ ID NO: 85) |
| #ET1-3E12 | VL | SLTTNY (SEQ ID NO: 86) | GKN (SEQ ID NO: 87) | NSRDSSGKHYV (SEQ ID NO: 88) |
| #P1-2A11 | VH | GFTFSSYA (SEQ ID NO: 65) | ISGSGGST (SEQ ID NO: 72) | AKDWGLVQLESGYDY (SEQ ID NO: 89) |
| #P1-2A11 | VL | SSNIGAGYD (SEQ ID NO: 90) | DNT (SEQ ID NO: 91) | AAWDESLNGQV (SEQ ID NO: 92) |
| #P4-2F1 | VH | GGSISSSDW (SEQ ID NO: 93) | IYHSGSP (SEQ ID NO: 94) | ARERVAPTVDGAFDV (SEQ ID NO: 95) |
| #P4-2F1 | VL | QSITTY (SEQ ID NO: 96) | AAS (SEQ ID NO: 97) | QQASSFPLT (SEQ ID NO: 98) |
| #T1-3G7 | VH | GYSFTNYW (SEQ ID NO: 99) | IYPGDSDT (SEQ ID NO: 100) | ARIKSYYDSSGYYL (SEQ ID NO: 101) |
| #T1-3G7 | VL | NIGSKS (SEQ ID NO: 102) | DDS (SEQ ID NO: 103) | QVWDSSSEEV (SEQ ID NO: 104) |
| #TT1-3C6 (and #E1-3F6) | VH | GFTFSSYA (SEQ ID NO: 65) | ISGSGGST (SEQ ID NO: 72) | ARRGFMDV (SEQ ID NO: 105) |
| #TT1-3C6 (and #E1-356) | VL | ILEAYY (SEQ ID NO: 106) | GEN (SEQ ID NO: 107) | NSRDSSGSHVV (SEQ ID NO: 108) |
| #TT1-3C8 | VH | GFTFNSFA (SEQ ID NO: 109) | ISGSGGST (SEQ ID NO: 72) | AKGHAFDI (SEQ ID NO: 110) |
| #TT1-3C8 | VL | QSLLHSDGKTY (SEQ ID NO: 111) | EVS (SEQ ID NO: 112) | MQSIQLPLT (SEQ ID NO: 113) |
| #TT1-3F5 | VH | GFTFSSYA (SEQ ID NO: 65) | ISGSGGST (SEQ ID NO: 72) | AKDKGGGFDP (SEQ ID NO: 114) |
| #TT1-3F5 | VL | SGSIASNY (SEQ ID NO: 115) | EDN (SEQ ID NO: 116) | QSYDSTSHV (SEQ ID NO: 117) |
| #TT5-3E2 | VH | GYSFTNYW (SEQ ID NO: 99) | IYPGDSDT (SEQ ID NO: 118) | ARPGYYYGSGSYYNVDY (SEQ ID NO: 119) |

TABLE 14-continued

Amino Acid Sequences of Heavy and Light Chains.

| Antibody | Variable region | CDR1 | CDR2 | CDR3 |
|---|---|---|---|---|
| #TT5-3E2 | VL | ELGDKF (SEQ ID NO: 120) | QDS (SEQ ID NO: 121) | QVWDSNGGPP (SEQ ID NO: 122) |

The present invention also features antibodies that have a specified percentage identity or similarity to the amino acid or nucleotide sequences of the huGITR antibodies described herein. For example, the antibodies may have 60%, 70%, 75%, 80%, 85%, 90%, 91%, 92%, 93%, 94%, 95%, 96%, 97%, 98%, 99%, or higher identity when compared a specified region or the full length of any one of the huGITR antibodies described herein. Sequence identity or similarity to the nucleic acids and proteins of the present invention can be determined by sequence comparison and/or alignment by methods known in the art. For example, sequence comparison algorithms (i.e. BLAST or BLAST 2.0), manual alignment or visual inspection can be utilized to determine percent sequence identity or similarity for the nucleic acids and proteins of the present invention.

As to amino acid sequences, one of skill in the art will readily recognize that individual substitutions, deletions or additions to a nucleic acid, peptide, polypeptide, or protein sequence which alters, adds, deletes, or substitutes a single amino acid or a small percentage of amino acids in the encoded sequence is collectively referred to herein as a "conservatively modified variant". In some embodiments the alteration results in the substitution of an amino acid with a chemically similar amino acid. Conservative substitution tables providing functionally similar amino acids are well known in the art. Such conservatively modified variants of the huGITR antibody disclosed herein may exhibit increased cross-reactivity to GITR in comparison to an unmodified GITR antibody.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$ and $IgG_4$ and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." VH and VL regions, which contain the CDRs, of the scFv antibodies are shown in Tables 1A-Table 13B.

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a GITR epitope when the equilibrium binding constant ($K_d$) is ≤10 µM, preferably ≤10 nM, more preferably ≤10 nM, and most preferably ≤100 pM to about 1 pM, as measured by assays such as radioligand binding assays or similar assays known to those skilled in the art.

An GITR protein of the invention, or a derivative, fragment, analog, homolog or ortholog thereof, may be utilized as an immunogen in the generation of antibodies that immunospecifically bind these protein components. A GITR protein or a derivative, fragment, analog, homolog, or ortholog thereof, coupled to a proteoliposome may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to GITR. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the GITR protein, with which it is normally reactive, and then add the human monoclonal antibody being tested to determine if the human monoclonal antibody being tested is inhibited in its ability to bind GITR. If the human monoclonal antibody being tested is inhibited then, in all likelihood, it has the same, or functionally equivalent, epitopic specificity as the monoclonal antibody of the invention. Screening of human monoclonal antibodies of the invention can be also carried out by utilizing GITR and determining whether the test monoclonal antibody is able to neutralize GITR.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which have a targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of GITR in a sample. The antibody can also be used to try to bind to and disrupt a GITR activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

In certain embodiments, an antibody of the invention may comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization to the brain, kidney, and/or liver is desired. In one exemplary embodiment, the altered antibodies of the invention exhibit reduced transport across the epithelium of kidney glomeruli from the vasculature. In another embodiment, the altered antibodies of the invention exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein. In certain exemplary embodiments, the antibodies, or fragments thereof, of the invention comprise an Fc domain having one or more of the following substitutions: V284E, H285E, N286D, K290E and S304D (EU numbering).

In some embodiments, mutations are introduced to the constant regions of the mAb such that the antibody dependent cell-mediated cytotoxicity (ADCC) activity of the mAb is altered. For example, the mutation is an LALA mutation in the CH2 domain. In one aspect, the bsAb contains mutations on one scFv unit of the heterodimeric mAb, which reduces the ADCC activity. In another aspect, the mAb contains mutations on both chains of the heterodimeric mAb, which completely ablates the ADCC activity. For example, the mutations introduced one or both scFv units of the mAb are LALA mutations in the CH2 domain. These mAbs with variable ADCC activity can be optimized such that the mAbs exhibits maximal selective killing towards cells that express one antigen that is recognized by the mAb, however exhibits minimal killing towards the second antigen that is recognized by the mAb.

In other embodiments, antibodies, for use in the diagnostic and treatment methods described herein have a constant region, e.g., an IgG$_1$ or IgG4 heavy chain constant region, which is altered to reduce or eliminate glycosylation. For example, an antibody of the invention may also comprise an Fc variant comprising an amino acid substitution which alters the glycosylation of the antibody. For example, said. Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228I) and a T299A mutation (EU numbering).

Exemplary amino acid substitutions which confer reduced or altered glycosylation are disclosed in International PCT Publication No, WO05/018572, which is incorporated by reference herein. In preferred embodiments, the antibodies, or fragments thereof, of the invention are modified to eliminate glycosylation. Such antibodies, or fragments thereof, may be referred to as "agly" antibodies, or fragments thereof, (e.g. "agly" antibodies). While not being bound by theory, it is believed that "agly" antibodies, or fragments thereof, may have an improved safety and stability profile in vivo. Exemplary agly antibodies, or fragments thereof, comprise an aglycosylated Fc region of an IgG4 antibody which is devoid of Fe-effector function thereby eliminating the potential for Fe mediated toxicity to the normal vital organs that express GITR. In yet other embodiments, antibodies, or fragments thereof, of the invention comprise an altered glycan. For example, the antibody may have a reduced number of fucose residues on an N-glycan at Asn297 of the Fe region, i.e., is afucosylated. In another embodiment, the antibody may have an altered number of sialic acid residues on the N-glycan at Asn297 of the Fe region. iii) Covalent Attachment The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun.

133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against GITR

Antibodies specifically binding a GITR protein or a fragment thereof of the invention can be administered for the treatment a GITR associated disease or disorder. A "GITR-associated disease or disorder" includes disease states and/or symptoms associated with a disease state, where increased levels of GITR and/or activation of cellular signaling pathways involving GITR are found. Exemplary GITR-associated disease or disorder include, but are not limited to, cancer and inflammatory diseases.

Many cancers overexpress GITR and the upregulation of GITR is associated with high risk prognostic factors. Overexpression of GITR or its ligand, GITR-L, in tumor cells can also indicate a mechanism by which the tumor cells evade anti-tumor immunity. Such cancers include solid tumor and hematologic tumor. Use of the antibody of the invention suppress or deplete Tregs and stimulate Teffs. In addition, the antibodies of the invention and increase the toxicity of NK cells and increase IFNγ production.

Antibodies of the invention, including bi-specific, polyclonal, monoclonal, humanized and fully human antibodies, may be used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the GITR protein.

Antibodies specifically binding a GITR protein or fragment thereof of the invention can be administered for the treatment of a cancer in the form of pharmaceutical compositions. Principles and considerations involved in preparing therapeutic compositions comprising the antibody, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine (e.g. IL-15), chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of GITR (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA includes Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Antibodies directed against a GITR protein (or a fragment thereof) may be used in methods known within the art relating to the localization and/or quantitation of a GITR protein (e.g., for use in measuring levels of the GITR protein within appropriate physiological samples, for use in diagnostic methods, for use in imaging the protein, and the like). In a given embodiment, antibodies specific to a GITR protein, or derivative, fragment, analog or homolog thereof, that contain the antibody derived antigen binding domain, are utilized as pharmacologically active compounds (referred to hereinafter as "Therapeutics").

An antibody specific for a GITR protein of the invention can be used to isolate a GITR polypeptide by standard techniques, such as immunoaffinity, chromatography or immunoprecipitation. Antibodies directed against a GITR protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Diagnostic Assays

The huGITR antibodies can be used diagnostically to, for example, monitor the development or progression of a immune cell disorder (e.g., CLL) as part of a clinical testing procedure to, e.g., determine the efficacy of a given treatment and/or prevention regimen.

In some aspects, for diagnostic purposes the huGITR antibody of the invention is linked to a detectable moiety, provides a way for detecting T cell exhaustion in a subject suffering from a cancer or a chronic infection.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cells that express GITR in a biological sample in vitro as well as in vivo. For example, in vitro techniques for detection of GITR include enzyme linked immunosorbent assays (ELISAs), Western blots, immunoprecipitations, and immunofluorescence. Furthermore, in vivo techniques for detection of GITR include introducing into a subject a labeled anti-GITR antibody. For example, the antibody can be labeled with a radioactive marker whose presence and location in a subject can be detected by standard imaging techniques. In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when an moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of GITR or a GITR-expressing cell in a biological sample. For example, the kit can comprise: a labeled compound or agent capable of detecting a cancer or tumor cell (e.g., an anti-GITR scFv or monoclonal antibody) in a biological sample; means for determining the amount of GITR in the sample; and means for comparing the amount of GITR in the sample with a standard. The standard is, in some embodiments, a non-cancer cell or cell extract thereof. The compound or agent can be packaged in a suitable container. The kit can further comprise instructions for using the kit to detect cancer in a sample.

Bi-Specific Antibodies

A bi-specific antibody (bsAb) is an antibody comprising two variable domains or scFv units such that the resulting antibody recognizes two different antigens. The present invention provides for bi-specific antibodies that recognize GITR and a second antigen. Exemplary second antigens include tumor associated antigens, cytokines and cell surface receptors. In some embodiments, the second antigen can be CAIX (carbonic anhydrase IX, or G250), IL-10 or CCR4. In some embodiments, the second antigen can be a cell surface receptor, wherein the cell surface receptor is PD-1, PDL1, CCR4, IL21R, BTLA, HVEM or TIM3. A bi-specific antibody of the present invention comprises a heavy chain and a light chain combination or scFv of the huGITR antibodies disclosed herein.

Construction of Bi-Specific Antibodies

Bi-specific antibodies of the present invention can be constructed using methods known art. In some embodiments, the bi-specific antibody is a single polypeptide wherein the two scFv fragments are joined by a long linker polypeptide, of sufficient length to allow intramolecular association between the two scFv units to form an antibody. In other embodiments, the bi-specific antibody is more than one polypeptide linked by covalent or non-covalent bonds.

In another embodiment, the bi-specific antibody is constructed using the "knob into hole" method (Ridgway et al., Protein Eng 7:617-621 (1996)). In this method, the Ig heavy chains of the two different variable domains are reduced to selectively break the heavy chain pairing while retaining the heavy-light chain pairing. The two heavy-light chain heterodimers that recognize two different antigens are mixed to promote heteroligation pairing, which is mediated through the engineered "knob into holes" of the CH3 domains.

In another embodiment, the bi-specific antibody can be constructed through exchange of heavy-light chain dimers from two or more different antibodies to generate a hybrid antibody where the first heavy-light chain dimer recognizes GITR and the second heavy-light chain dimer recognizes a second antigen. The mechanism for heavy-light chain dimer is similar to the formation of human IgG4, which also functions as a bispecific molecule. Dimerization of IgG heavy chains is driven by intramolecular force, such as the pairing the CH3 domain of each heavy chain and disulfide bridges. Presence of a specific amino acid in the CH3 domain (R409) has been shown to promote dimer exchange and construction of the IgG4 molecules. Heavy chain pairing is also stabilized further by interheavy chain disulfide bridges in the hinge region of the antibody. Specifically, in IgG4, the hinge region contains the amino acid sequence Cys-Pro-Ser-Cys (in comparison to the stable IgG1 hinge region which contains the sequence Cys-Pro-Pro-Cys) at amino acids 226-230. This sequence difference of Serine at position 229 has been linked to the tendency of IgG4 to form novel intrachain disulfides in the hinge region (Van der Neut Kolfschoten, M. et al., 2007, *Science* 317:1554-1557 and Labrijn, A. F. et al, 2011, *Journal of immunol* 187:3238-3246).

Therefore, bi-specific antibodies of the present invention can be created through introduction of the R409 residue in the CH3 domain and the Cys-Pro-Ser-Cys sequence in the hinge region of antibodies that recognize GITR or a second antigen, so that the heavy-light chain dimers exchange to produce an antibody molecule with one heavy-light chain dimer recognizing GITR and the second heavy-light chain dimer recognizing a second antigen, wherein the second antigen is any antigen disclosed herein. Known IgG4 molecules may also be altered such that the heavy and light chains recognize GITR or a second antigen, as disclosed herein. Use of this method for constructing the bi-specific antibodies of the present invention may be beneficial due to the intrinsic characteristic of IgG4 molecules wherein the Fc region differs from other IgG subtypes in that it interacts poorly with effector systems of the immune response, such as complement and Fc receptors expressed by certain white blood cells. This specific property makes these IgG4-based bi-specific antibodies attractive for therapeutic applications, in which the antibody is required to bind the target(s) and functionally alter the signaling pathways associated with the target(s), however not trigger effector activities.

In some embodiments, mutations are introduced to the constant regions of the bsAb such that the antibody dependent cell-mediated cytotoxicity (ADCC) activity of the bsAb is altered. For example, the mutation is an LALA mutation in the CH2 domain. In one aspect, the bsAb contains mutations on one scFv unit of the heterodimeric bsAb, which reduces the ADCC activity. In another aspect, the bsAb contains mutations on both chains of the heterodimeric bsAb, which completely ablates the ADCC activity. For example, the mutations introduced one or both scFv units of the bsAb are LALA mutations in the CH2 domain. These bsAbs with variable ADCC activity can be optimized such that the bsAbs exhibits maximal selective killing towards cells that express one antigen that is recognized by the bsAb, however exhibits minimal killing towards the second antigen that is recognized by the bsAb.

The bi-specific antibodies disclosed herein may be useful in treatment of diseases or medical conditions, for example, cancer. The bi-specific antibodies of the present invention may be particularly useful in diseases or medical conditions that are associated with increased Tregs. I Methods of Treatment The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of GITR. For example, the methods are used to treat, prevent or alleviate a symptom cancer. Alternatively, the methods are used to treat, prevent or alleviate a symptom of a cancer in which GITR plays a negative regulatory role in T cell response. Alternatively, the methods are used to treat, prevent or alleviate a symptom of a solid tumor such as breast cancer, lung cancer, ovarian cancer, prostate cancer, colon cancer, cervical cancer, brain cancer, skin cancer, liver cancer, pancreatic cancer or stomach cancer. Additionally, the methods of the invention are used to treat hematologic cancers such as leukemia and lymphoma. Alternatively, the methods are used to treat, prevent or alleviate a symptom of a cancer that has metastasized.

Accordingly, in one aspect, the invention provides methods for preventing, treating or alleviating a symptom cancer or a cell proliferative disease or disorder in a subject by administering to the subject a monoclonal antibody, scFv antibody of the invention or bi-specific antibody of the invention. For example, a huGITR antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited, Treg activity is decreased, Teff activity is increased, or NK-cell cytotoxicity in increased by contacting a cell with a GITR antibody of the invention. The cell is any cell that expresses GITR. For example the cell is T cell or an NK cell.

Also included in the invention are methods of increasing or enhancing an immune response to an antigen. An immune response is increased or enhanced by administering to the subject a monoclonal antibody or scFv antibody of the invention. The immune response is augmented for example by augmenting antigen specific T effector function. The antigen is a viral (e.g. HIV), bacterial, parasitic or tumor antigen. The immune response is a natural immune response. By natural immune response is meant an immune response that is a result of an infection. The infection is a chronic infection. Increasing or enhancing an immune response to an antigen can be measured by a number of methods known in the art. For example, an immune response can be measured by measuring any one of the following: T cell activity, T cell proliferation, T cell activation, production of effector cytokines, and T cell transcriptional profile.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

Combinatory Methods

The invention provides treating cancer in a patient by administering two antibodies that bind to the same epitope of the GITR protein or, alternatively, two different epitopes of the GITR protein. Alternatively, the cancer is treated by administering a first antibody that binds to GITR and a second antibody that binds to a protein other than GITR. For example, the other protein other than GITR may include, but is not limited to, PD-1, PD-L1, CAIX, CCR4 and IL-10. For example, the other protein other than GITR is a tumor-associated antigen.

In some embodiments, the invention provides administration of a huGITR antibody alone or with an additional antibody that recognizes another protein other than GITR, with cells that are capable of effecting or augmenting an immune response. For example, these cells may be peripheral blood mononuclear cells (PBMC), or any cell type that is found in PBMC, e.g., cytotoxic T cells, macrophages, and natural killer (NK) cells.

Additionally, the invention provides administration of an antibody that binds to the GITR protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1: Isolation of Anti-GITR Antibodies

Identification of Here is described isolation of thirteen anti-GITR monoclonal antibodies. Panning with hGITR-mIg was performed with the Mehta I/II phage display libraries for three rounds with different antigen concentrations and wash conditions. Panning with mGITR-his was performed for two rounds with different antigen concentrations and wash conditions. ELISA assays were then performed to screen single clones from round two and three with 2 ug/ml of hGITR-mIgG2a or mGITR-His from Round 2. ELISA positive clones were sequenced and confirmed with a second ELISA assay including negative control as described in FIG. 1. Forty three unique clones were identified.

Clones were further tested for binding to hGITR using MSD (meso scale discovery system) at two different concentrations of the hGITR-mIgG2a antigen and four different concentrations of PEG purified anti-GITR phage-AB (FIG. 2). A second experiment was performed testing eight concentrations of hGITR-mIg and a constant number of PEG purified anti-GITR phage-AB (FIG. 3).

Example 2: Characterization of ELISA Positive and FACS Positive Clones from hGITR and mGITR Panning In total, twenty nine unique clones were identified after initial ELISA and FACS screening using hGITR-mIg panning. After ELISA analysis ten of these clones were identified as binding to anti-hGITR but not hGITR-His. Nineteen of these clones bound both hGITR-mIg and His, with four of these having weak binding efficiency. Fifteen clones were positive in FACS analysis, with three having weaker binding than the others. There were also six total ELISA unique positive clones after two rounds of mGITR-His panning. Four of these clones bound to anti-mGITR-His only, and two bound to both mGITR-His and hGITR-his. One scFV was selected against mGITR but it strongly reacts with hGITR-mIg and –His.

Example 3: Characterization of Anti-GITR Antibodies

Binding of anti-GITR was tested using four different concentrations of anti-GITR phage-AB. In addition, stable CHO cells expressing either GITR or CA9 were tested for anti-GITR antibody binding. Percentage of FITC positive CHO cells using FACS analysis to assay GITR binding is shown in FIG. 4. A third FACS GITR binding assay was performed using single concentration with phage supernatant from single colonies (FIG. 5). This analysis revealed anti-GITR antibodies that bound GITR expressing CHO cells and not CA9 expressing CHO cells. Those positive for GITR binding were selected for further ELISA analysis using a single concentration of phage supernatant from single colonies (FIG. 6). A final list of selected anti-GITR antibodies that were both flow cytometry and ELISA positive are listed in FIG. 7.

Figure 8:
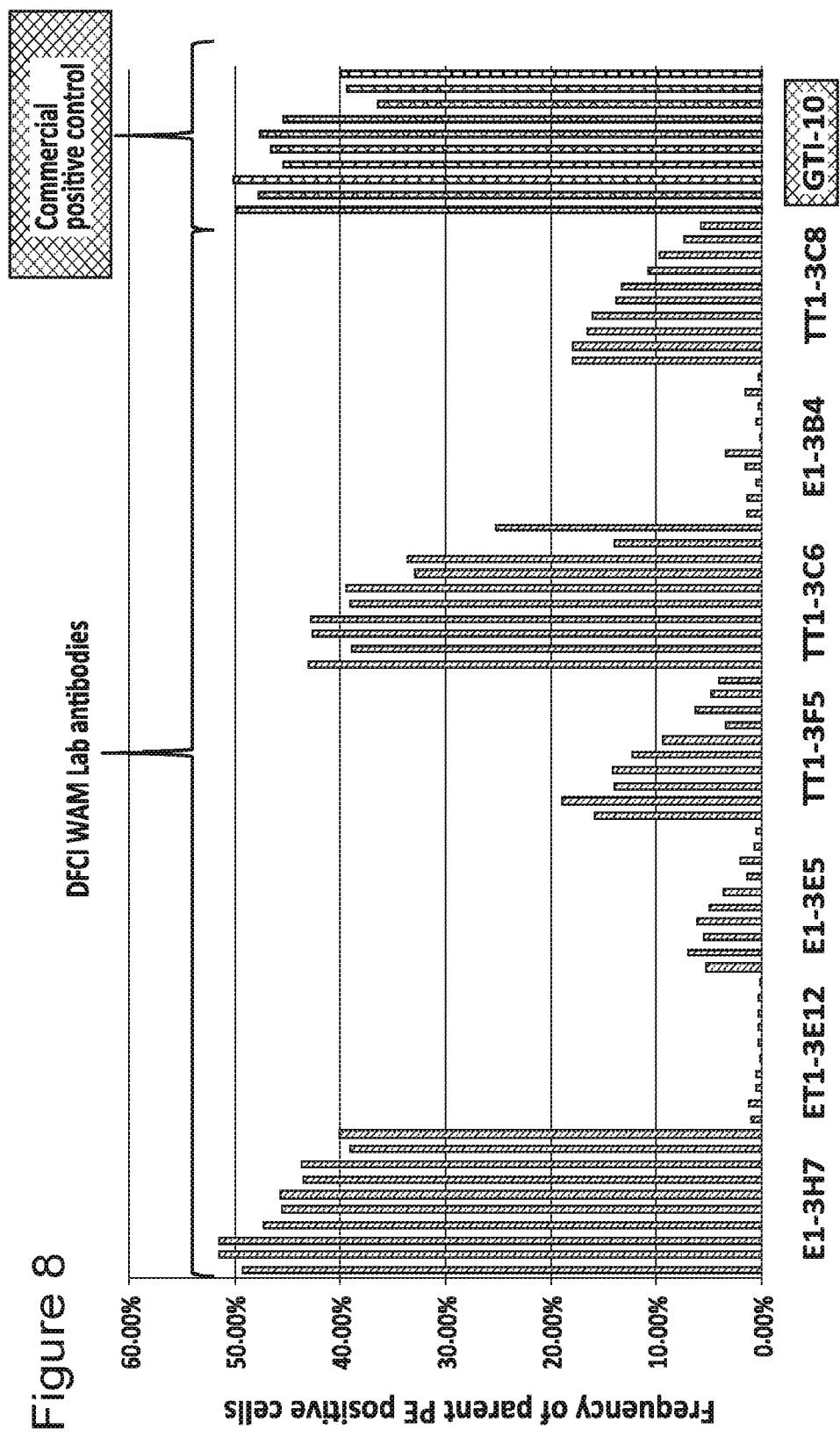
FIG. 8 is a graph showing GITR binding of anti-GITR antibodies expressed in full IgG1-Fc(LALA) mutant format as analyzed by flow cytomtry assays. Anti-GITR mAb binding to the GITR(+) CHO cell lines were tested by 5-point 2× serial dilutions in duplicates.
Figure 9:
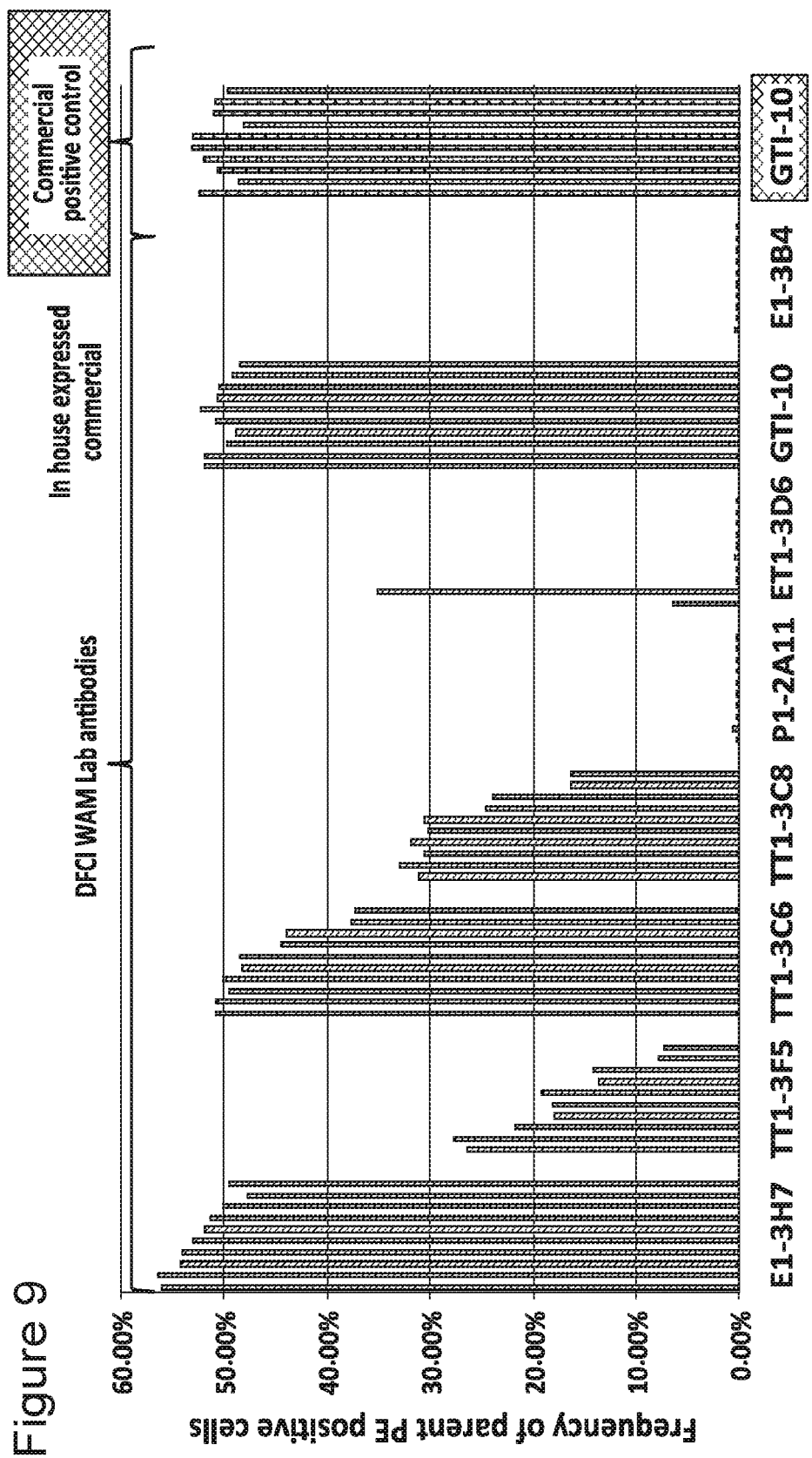
FIG. 9 is a graph showing another flow cytometry analysis of anti-GITR IgG1-Fc(LALA) antibodies binding to the cell surface expressed GITR. Anti-GITR mAb binding to the GITR(+) CHO cell lines were tested by 5-point 2× serial dilutions in duplicates.
Figure 10A:
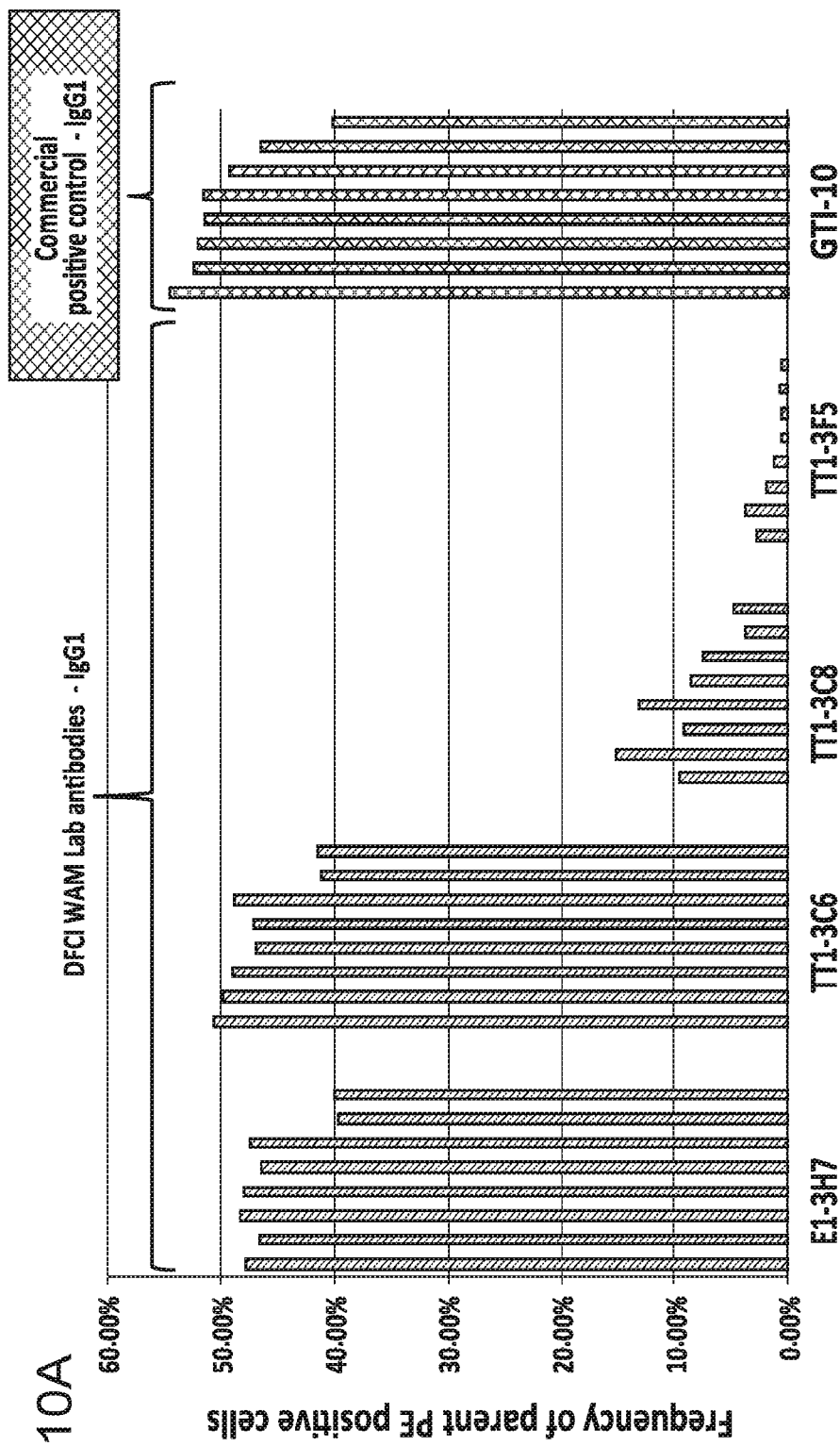
FIG. 10 demonstrates GITR binding ability of representative anti-GITR IgG1 antibodies expressed in IgG 1-Fc (LALA) format (Panel A) or in IgG4 format (Panel B), analyzed by flow cytometry. Anti-GITR mAb binding to the GITR(+) CHO cell lines were tested by 4-point 2× serial dilutions in duplicates.

Example 4: Construction and Expression of Anti-GITR mAb in IGG1-FC(LALA) Mutant Format and IGG4 Format VH and VL fragments of our newly discovered anti-GITR phage scFv antibodies were PCR cloned into mammalian expression vector TCAE to be expressed either in IgG1 Fc (LALA) mutant form or in IgG4 form, both formats with reduced or minimal ADCC activities. Upon in vitro transfection of 293F cells, cell supernatants were harvested and IgG concentration were quantitated by human IgG quantitation assays. The supernatants were then used to test GITR binding activities of these IgG mAbs to GITR(+) CHO cells using flow cytometry. Results provided in FIGS. 8-10 demonstrate that most of the anti-GITR antibodies retain their GITR binding activities upon conversion to IgG format.

Example 5: Binding Competition Between GITR Ligand and Anti-GITR Antibodies

Figure 11:
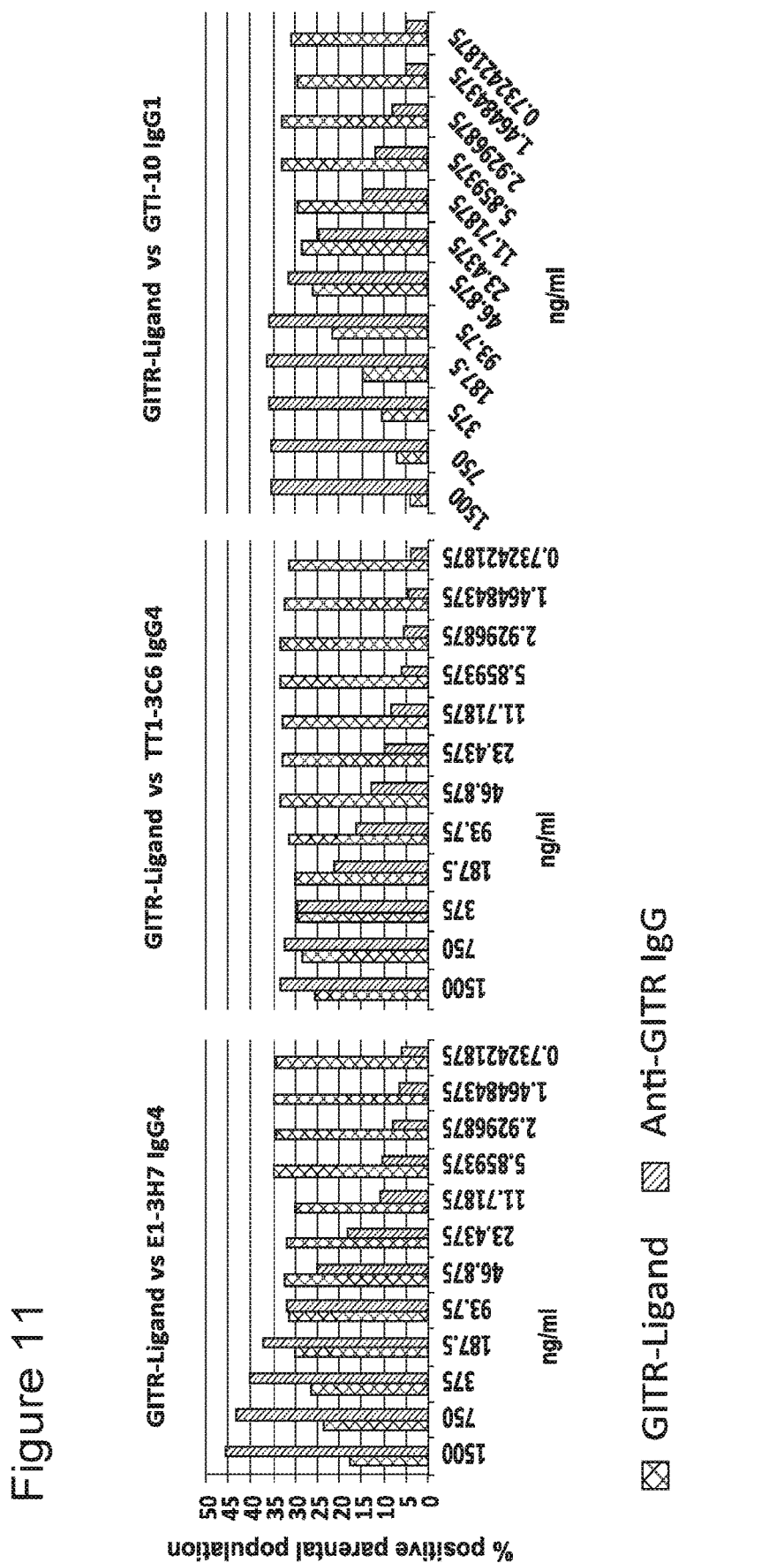
FIG. 11 illustrates binding competition between GITR ligand at 47 ng/ml and 10-point 2× serial dilution of anti-GITR E1-3H7 IgG4, TT1-3C6 IgG4, or commercial GTI-10 IgG1 antibodies.
Figure 12:
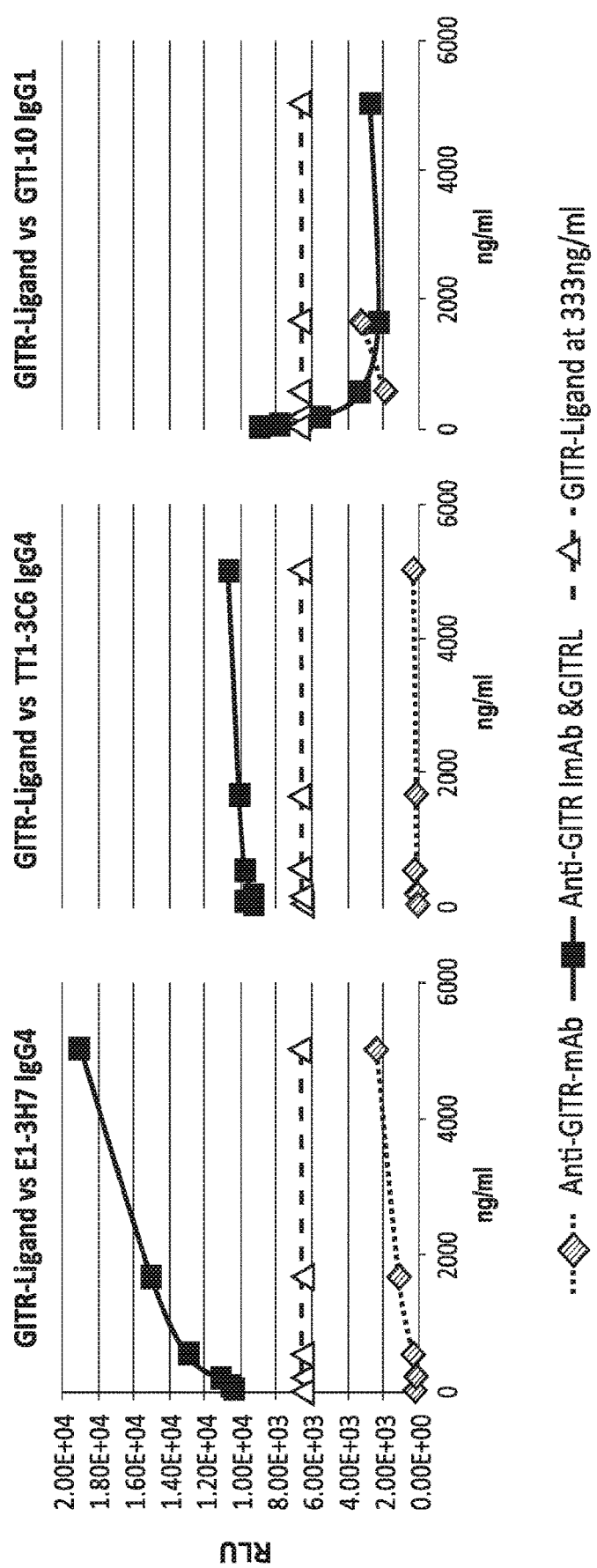
FIG. 12 illustrates that anti-GITR E1-3H7 IgG4 or TT1-3C6 synergistically increases GITR ligand induced luciferase expression in an in vitro assay with GloResponse™ NF-κB-luc2P/GITR Jurkat cells by Promega.

In order to further characterize our newly discovered anti-GITR antibodies, a competition binding assay was performed between increasing amount of purified anti-GITR E1-3H7 IgG4 or TT1-3C6 IgG4 with a constant concentration of GITR ligand by flow cytometry, respectively. FIG. 11 shows that the binding of GITR ligand (detected by Alexa 488 labeled anti-HA-tag) is reduced by increasing amounts of anti-GITR antibodies (detected by PE-labeled mouse-anti-human antibody, a feature shared with the commercial GTI10 antibody although to a lesser degree. When NF-κB-luc2P/GITR Jurkat reporter cells were incubated with increasing concentration of anti-GITR E1-3H7 IgG4 or TT1-3C6 IgG4 antibodies together with a constant concentration of GITR ligand, the luciferase activities increased to the level well above when the cells incubated with the ligand or anti-GITR antibodies alone, a feature not shared by the commercial GTI10 antibody (FIG. 12). These results indicate that anti-GITR E1-3H7 IgG4 or TT1-3C6 may synergistically increase GITR ligand induced luciferase expression in GloResponse™ NF-κB-luc2P/GITR Jurkat cells by Promega.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated humanized monoclonal antibody or antigen-binding fragment thereof that binds to the human-glucocorticoid-induced tumor necrosis factor receptor (GITR) comprising:
   a. a variable heavy chain region comprising the amino acid sequence of SEQ ID NO: 2, and a variable light chain region comprising the amino acid sequence of SEQ ID NO: 4;
   b. a variable heavy chain region comprising the amino acid sequence of SEQ ID NO: 6, and a variable light chain region comprising the amino acid sequence of SEQ ID NO: 8;
   c. a variable heavy chain region comprising the amino acid sequence of SEQ ID NO: 10, and a variable light chain region comprising the amino acid sequence of SEQ ID NO: 12;
   d. a variable heavy chain region comprising the amino acid sequence of SEQ ID NO: 14, and a variable light chain region comprising the amino acid sequence of SEQ ID NO: 16;
   e. a variable heavy chain region comprising the amino acid sequence of SEQ ID NO: 18, and a variable light chain region comprising the amino acid sequence of SEQ ID NO: 20;
   f. a variable heavy chain region comprising the amino acid sequence of SEQ ID NO: 22, and a variable tight chain region comprising the amino acid sequence of SEQ ID NO: 24;
   g. a variable heavy chain region comprising the amino acid sequence of SEQ ID NO: 26, and a variable light chain region comprising the amino acid sequence of SEQ ID NO: 28;
   h. a variable heavy chain region comprising the amino acid sequence of SEQ ID NO: 30, and a variable light chain region comprising the amino acid sequence of SEQ ID NO: 32;
   i. a variable heavy chain region comprising the amino acid sequence of SEQ ID NO: 34, and a variable light chain region comprising the amino acid sequence of SEQ ID NO: 36;
   j. a variable heavy chain region comprising the amino acid sequence of SEQ ID NO: 38, and a variable light chain region comprising the amino acid sequence of SEQ ID NO: 40;
   k. a variable heavy chain region comprising the amino acid sequence of SEQ ID NO: 42, and a variable light chain region comprising the amino acid sequence of SEQ ID NO: 44;
   l. a variable heavy chain region comprising the amino acid sequence of SEQ ID NO: 46, and a variable light chain region comprising the amino acid sequence of SEQ ID NO: 48; or
   m. a variable heavy chain region comprising the amino acid sequence of SEQ ID NO: 50, and a variable light chain region comprising the amino acid sequence of SEQ ID NO: 52.

2. An isolated humanized monoclonal antibody or antigen-binding fragment thereof, wherein the antibody or antigen-binding fragment comprises:
   (a) a variable heavy chain complementarity determining region 1, 2, and 3 (VH-CDR) comprising the amino acid sequences of SEQ ID NO. 53, 54 and 55, respectively; and, a variable light chain complementarity determining region 1, 2 and 3 (VL-CDR) comprising the amino acid sequences of SEQ ID NO. 56, 57, and 58;
   (b) a variable heavy chain complementarity determining region 1, 2, and 3 (VH-CDR) comprising the amino acid sequences of SEQ ID NO. 59, 60, and 61, respectively; and, a variable Sight chain complementarity determining region 1, 2 or 3 (VL-CDR) comprising the amino acid sequences of SEQ ID NO. 62, 63, and 64;
   (c) a variable heavy chain complementarity determining region 1, 2, and 3 (VH-CDR) comprising the amino acid sequences of SEQ ID NO. 65, 66, and 67, respectively; and, a variable light chain complementarity determining region 1, 2 and 3 (VL-CDR) comprising the amino acid sequences of SEQ ID NO, 68, 69, and 70;
   (d) a variable heavy chain complementarity determining region 1, 2, and 3 (VH-CDR) comprising the amino acid sequences of SEQ ID NO. 71, 72, and 73, respectively; and, a variable light chain complementarity determining region 1, 2 and 3 (VL-CDR) comprising the amino acid sequences of SEQ ID NO. 74, 75, and 76;
   (e) a variable heavy chain complementarity' determining region 1, 2, and 3 (VH-CDR) comprising the amino acid sequences of SEQ ID NO. 77, 78, and 79, respectively; and, a variable light chain complementarity determining region 1, 2 and 3 (VL-CDR) comprising the amino acid sequences of SEQ ID NO. 80, 81, and 82;
   (f) a variable heavy chain complementarity determining region 1, 2, and 3 (VH-CDR) comprising the amino acid sequences of SEQ ID NO. 83, 84, and 85, respectively; and, a variable light chain complementarity determining region 1, 2 and 3 (VL-CDR) comprising the amino acid sequences of SEQ ID NO. 86, 87, and 88;

(g) a variable heavy-chain complementarity' determining region 1, 2, and 3 (VH-CDR) comprising the amino acid sequences of SEQ ID NO. 65, 72, and 89, respectively; and, a variable Sight chain complementarity' determining region 1, 2 and 3 (VL-CDR) comprising the amino acid sequences of SEQ ID NO. 90, 91, and 92;

(h) a variable heavy chain complementarity determining region 1, 2, and 3 (VH-CDR) comprising the amino acid sequences of SEQ ID NO. 93, 94, and 95, respectively; and, a variable light chain complementarity' determining region 1, 2 and or 3 (VL-CDR) comprising the amino acid sequences of SEQ ID NO. 96, 97, and 98;

(i) a variable heavy chain complementarity determining region 1, 2, and 3 (VH-CDR) comprising the amino acid sequences of SEQ ID NO. 99, 100, and 101, respectively; and, a variable light chain complementarity determining region L 2 and 3 (VL-CDR) comprising the amino acid sequences of SEQ ID NO. 102, 103, and 104;

(j) a variable heavy chain complementarity determining region 1, 2, and 3 (VH-CDR) comprising the amino acid sequences of SEQ ID NO. 65, 72, and 105, respectively; and, a variable light chain complementarity determining region 1, 2 and 3 (VL-CDR) comprising the amino acid sequences of SEQ ID NO. 106, 107, and 108;

(k) a variable heavy chain complementarity determining region 1, 2, and 3 (VH-CDR) comprising the amino acid sequences of SEQ ID NO. 109, 72, and 110, respectively; and, a variable light chain complementarity' determining region 1, 2 and 3 (VL-CDR) comprising the amino acid sequences of SEQ ID NO. III, 112, and 113;

(l) a variable heavy chain complementarity' determining region 1, 2, and 3 (VH-CDR) comprising the amino acid sequences of SEQ ID NO. 65, 72, and 114, respectively; and, a variable light chain complementarity determining region 1, 2 and 3 (VL-CDR) comprising the amino acid sequences of SEQ ID NO. 115, 116, and 117; or (m) a variable heavy chain complementarity determining region 1, 2, and 3 (VH-CDR) comprising the amino acid sequences of SEQ ID NO. 101, 118, and 119, respectively; and, a variable light chain complementarity determining region 1, 2 and 3 (VL-CDR) comprising the amino acid sequences of SEQ ID NO. 120, 121, and 122, wherein said antibody or antibody binding fragment binds human-glucocorticoid-induced tumor necrosis factor receptor (GITR).

3. The antibody of claim 1, wherein said antibody is monovalent or bivalent.

4. The antibody of claim 1, wherein said antibody is a single chain antibody.

5. The antibody of claim 1, wherein said antibody has a binding affinity within the range of $10^{-5}$ M to $10^{-12}$ M.

6. The antibody of claim 1, wherein said antibody has a IgG4 heavy chain constant region.

7. The antibody of claim 1, wherein the Fe region contains mutations at amino acid positions 234 and 235.

8. The antibody of claim 7, wherein e imitations are L234A and L235A.

9. The antibody according to claim 1 wherein said antibody is a bi-specific antibody that also hinds to a tumor-associated antigen, a cytokine or a cell surface receptor.

10. The antibody according to any one of preceding claims linked to a therapeutic agent.

11. The antibody of claim 10, wherein said therapeutic agent is a toxin, a radiolabel, a siRNA, a small molecule, or a cytokine.

12. A cell producing the antibody of any one of claims 1-11.

13. A method of depleting regulatory T-cells in a subject, comprising administering to a subject in need thereof a composition comprising an antibody according to any one of claims 1-11.

14. A method of augmenting an immune response to an antigen comprising administering to a subject in need thereof a composition comprising an antibody of any one of claims 1-11.

15. The method of claim 14, wherein said antigen is a viral antigen, a bacterial antigen or a tumor associated antigen.

16. The method of claim 14, wherein said administration of aid antibody causes an increase in antigen specific T cell activity.

17. The method of claim 14, wherein said administration of said antibody causes an increase NK cell cytoxicity.

18. The method of claim 14, further comprising administering to said subject IL-15.

19. A method of treating or alleviating a symptom of cancer, comprising administering to a subject in need thereof a composition comprising an antibody according to any one of claims 1-11.

20. The method of claim 19, wherein said cancer is a cancer in which GITR or its ligand, GITR-L, is overexpressed.

21. The method of claim 20, comprising further administering to said subject a cytokine or a chemotherapeutic agent.

22. The method of claim 21, wherein the cytokine is IL-15.

23. A nucleic acid comprising the nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51.

24. A nucleic acid encoding the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

25. A polypeptide comprising the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52.

26. A vector comprising the nucleic acid claim 23 or 24.

27. An isolated cell comprising the vector of claim 26.

* * * * *